US008663605B2

(12) United States Patent
Kaftan et al.

(10) Patent No.: US 8,663,605 B2
(45) Date of Patent: Mar. 4, 2014

(54) AGENT FOR FIBERS CONTAINING KERATIN, COMPRISING AT LEAST ONE SPECIFIC AMPHIPHILIC CATIONIC POLYMER, AT LEAST ONE CATIONIC STYLING POLYMER THAT IS DIFFERENT THEREFROM AND AT LEAST ONE FILM-FORMING NON-IONIC AND/OR STABILIZING NON-IONIC POLYMER

(75) Inventors: Pamela Kaftan, Hamburg (DE); Burkhard Mueller, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/027,564

(22) Filed: Feb. 15, 2011

(65) Prior Publication Data

US 2011/0132389 A1    Jun. 9, 2011

Related U.S. Application Data

(63) Continuation of application No. PCT/EP2009/059357, filed on Jul. 21, 2009.

(30) Foreign Application Priority Data

Aug. 18, 2008 (DE) .......................... 10 2008 038 110
Nov. 28, 2008 (DE) .......................... 10 2008 059 480

(51) Int. Cl.
| | | |
|---|---|---|
| *A01N 25/02* | (2006.01) | |
| *A61K 9/12* | (2006.01) | |
| *A61K 8/73* | (2006.01) | |
| *A61K 8/81* | (2006.01) | |
| *A61Q 5/06* | (2006.01) | |
| *A45D 7/04* | (2006.01) | |

(52) U.S. Cl.
USPC ........ 424/43; 424/70.13; 424/70.15; 132/203

(58) Field of Classification Search
USPC ....................... 424/43, 70.13, 70.15; 132/203
See application file for complete search history.

(56) References Cited

U.S. PATENT DOCUMENTS

| | | | |
|---|---|---|---|
| 3,753,968 A | 8/1973 | Ward | |
| 6,235,913 B1 | 5/2001 | Raths et al. | |
| 6,383,477 B1 | 5/2002 | Lede et al. | |
| 6,852,815 B1 | 2/2005 | Chuang et al. | |
| 7,332,466 B2 | 2/2008 | Schmid et al. | |
| 2006/0013785 A1* | 1/2006 | Lauscher et al. ............. | 424/70.9 |

FOREIGN PATENT DOCUMENTS

| | | |
|---|---|---|
| AU | 730455 B2 | 5/2000 |
| DE | 3139438 A1 | 4/1983 |
| DE | 19756454 C1 | 6/1999 |
| DE | 19937434 A1 | 7/2000 |
| DE | 10240757 A1 | 7/2003 |
| WO | 2006050788 A1 | 5/2006 |

OTHER PUBLICATIONS

Rigoletto et al. Cosmetic Science Technology, 2007, 142-156 (1st page In IDS submitted on May 13, 2011).*
International Cosmetic Ingredient Dictionary & Handbook. The Cosmetic Toiletry and Fragrance Association, 7th Edition, 1997.
Rigoletto, Raymond et al. "Polyquatemium-69: A New Fixative Polymer with Enhanced Styling Benefits," Cosmetic Science Technology, Jan. 1, 2007, p. 142.
"Aquastyle 300." ISP Corporation, Dec. 6, 2006, Retrieved from http://www.ispjapan.co.jp/pc_refguide/pdf/AquaStyle_300_jp, pp. 71, 82-93, on Dec. 3, 2009.

* cited by examiner

*Primary Examiner* — Gina C Justice
*Assistant Examiner* — Genevieve S Alley
(74) *Attorney, Agent, or Firm* — Ingrassia Fisher & Lorenz, P.C.

(57) ABSTRACT

Agent for treating fibers containing keratin, in particular human hair, having in a cosmetically acceptable carrier, (a) at least one amphiphilic, cationic polymer comprising at least one structural unit of formulae (I) to (IV), wherein $R^1$ and $R^4$ are independently hydrogen or a methyl group; $X^1$ and $X^2$ are independently oxygen or a NH group; $A^1$ and $A^2$ are independently ethane-1,2-diyl, propane-1,3-diyl or butane-1,4-diyl; $R^2$, $R^3$, $R^5$ and $R^6$ are independently a ($C_1$ to $C_4$)-alkyl group; $R^7$ is a ($C_8$ to $C_{30}$)-alkyl group; (b) at least one other film-forming cationic and/or stabilizing cationic polymer; and (c) at least one film-forming non-ionic and/or stabilizing non-ionic polymer. The invention also relates to the use of the agent for temporarily styling hair and for haircare, particularly as an aerosol hairspray or aerosol mousse.

14 Claims, No Drawings

AGENT FOR FIBERS CONTAINING KERATIN, COMPRISING AT LEAST ONE SPECIFIC AMPHIPHILIC CATIONIC POLYMER, AT LEAST ONE CATIONIC STYLING POLYMER THAT IS DIFFERENT THEREFROM AND AT LEAST ONE FILM-FORMING NON-IONIC AND/OR STABILIZING NON-IONIC POLYMER

CROSS REFERENCE TO RELATED APPLICATIONS

The present application is a continuation of International Patent Application No. PCT/EP2009/059357 filed 21 Jul. 2009, which claims priority to German Patent Application Nos. 10 2008 059 480.6 filed 28 Nov. 2008 and 10 2008 038 110.1 filed 18 Aug. 2008.

The present invention relates to agents for treating hair, wherein the agent contains a combination of at least one amphiphilic, cationic polymer with at least one different cationic styling polymer and at least one film-forming non-ionic and/or setting non-ionic polymer, use of these agents for the temporary shaping and/or care of keratin-containing fibers, and aerosol hair sprays/foams based on these agents.

Keratin-containing fibers generally include all animal hair (e.g., wool, horsehair, angora hair, furs, feathers and products or fabrics produced from them). However, the keratinic fibers preferably concern human hair.

Today, a suitably looking hairstyle is generally regarded as an essential part of a well groomed appearance. Based on actual fashion trends, time and again hairstyles are considered chic, which, for many types of hair, can only be formed or sustained over a longer period of up to several days by use of certain consolidating materials. Thus, hair treatments that provide a permanent or temporary hairstyling play an important role. Temporary styling intended to provide a good hold without compromising the healthy appearance of the hair, such as the gloss, can be obtained, for example, by use of hairsprays, hair waxes, hair gels, hair foams, setting lotions, etc.

Suitable compositions for temporary hairstyling usually contain synthetic polymers as the styling component. Preparations containing a dissolved or dispersed polymer can be applied onto hair by propellants or by a pumping mechanism. Hair gels and hair waxes, however, are generally not applied directly on the hair, but rather dispersed with a comb or by hand.

An important property of an agent for the temporary styling of keratin fibers, also referred to as styling agents, consists in giving the treated fibers the strongest possible hold for the shape created. If the keratinic fibers concern human hair, then one also speaks of a strong hairstyle hold or a high degree of hold of the styling agent. Styling hold is determined by the type and amount of the synthetic polymer used; however, there may also be an influence from other components in the styling agent.

In addition to a high degree of hold, styling agents must fulfill a whole series of additional requirements. These requirements can be broadly subdivided into properties on the hair, properties of the formulation in question (e.g., properties of the foam, the gel or the sprayed aerosol), and properties concerning the handling of the styling agent, with particular importance attached to the properties on the hair. These include moisture resistance, low stickiness and a balanced conditioning effect. Furthermore, a styling agent should be universally applicable for as many types of hair as possible.

In an attempt to meet the various requirements, various synthetic polymers have already been developed and are being used in styling agents. These polymers can be subdivided into cationic, anionic, non-ionic and amphoteric film-forming and/or setting polymers. Ideally these polymers form a polymer film when applied to hair, imparting a strong hold to the hairstyle while also being sufficiently flexible so as to not break under stress. If the polymer film is too brittle, film plaques develop (i.e., residues that are shed with movement of the hair and give the impression that the user of the styling agent has dandruff).

Developing styling agents that have all the desired properties still presents problems. This is particularly true for the combination of strong hold and simple, uniform application onto the keratin-containing fibers.

Accordingly, the present invention provides an agent for temporary shaping and/or care of keratinic fibers having a high degree of hold or high care action, and particularly possessing an excellent handleability during application onto the keratin-containing fibers.

It has now been surprisingly found that this can be achieved by a combination of specific polymers.

Accordingly, a first subject matter of the present invention is an agent for treating keratin-containing fibers, especially human hair, comprising in a cosmetically acceptable carrier (a) at least one amphiphilic, cationic polymer containing at least one structural unit according to Formula (I), at least one structural unit according to Formula (II), at least one structural unit according to Formula (III) and at least one structural unit according to Formula (IV),

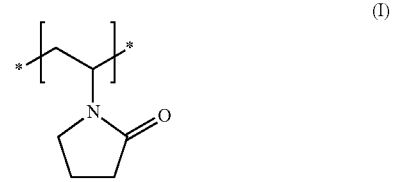

(I)

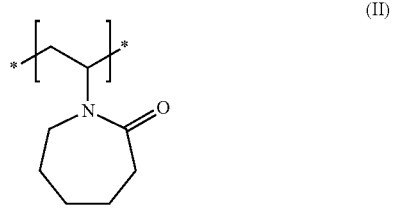

(II)

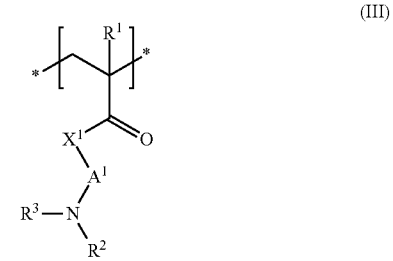

(III)

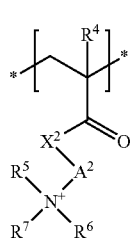

wherein
- $R^1$ and $R^4$ are, independently of one another, a hydrogen atom or a methyl group,
- $X^1$ and $X^2$ are, independently of one another, an oxygen atom or an NH group,
- $A^1$ and $A^2$ are, independently of one another, an ethane-1,2-diyl, propane-1,3-diyl or butane-1,4-diyl group,
- $R^2$, $R^3$, $R^5$ and $R^6$ are, independently of one another, a ($C_1$ to $C_4$) alkyl group,
- $R^7$ is a ($C_8$ to $C_{30}$) alkyl group, and (b) at least one additional film-forming cationic and/or setting cationic polymer, and (c) at least one film-forming non-ionic and/or setting non-ionic polymer.

Film-forming polymers refer to those polymers that, on drying, leave a continuous film on the skin, hair or nails. These film-formers can be used in a wide variety of cosmetic products, such as make up masks, make up, hair sets, hair sprays, hair gels, hair waxes, hair conditioners, shampoos or nail varnishes. Those polymers are particularly preferred which are sufficiently soluble in alcohol or water/alcohol mixtures so that they are present in completely dissolved form in agents according to the invention. Film-forming polymers can be of synthetic or of natural origin.

According to the invention, film-forming polymers further refer to those polymers that, when used in concentrations of 0.01 to 20 wt. % in aqueous, alcoholic or aqueous alcoholic solution, are able to separate out a transparent polymer film on the hair.

Setting polymers contribute to the hold and/or creation of hair volume and hair body of the whole hairstyle. These polymers are also film-forming polymers, and are therefore generally typical substances for styling hair treatment compositions such as hair sets, hair foams, hair waxes, and hair sprays. Film formation can be in completely selected areas and bond only some fibers together.

The curl-retention test is frequently used as a test method for the setting action.

In the above Formulae and all Formulae below, the symbol * represents a chemical bond that stands for a free valence of the corresponding structural fragment.

To compensate for the positive charge on the polymer in the agent, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, and triflate.

Exemplary ($C_1$ to $C_4$) alkyl groups are methyl, ethyl, propyl, isopropyl, butyl, sec-butyl, isobutyl, and tert-butyl.

Exemplary ($C_8$ to $C_{30}$) alkyl groups are octyl (capryl), decyl (caprinyl), dodecyl (lauryl), tetradecyl (myristyl), hexadecyl (cetyl), octadecyl (stearyl), eicosyl (arachyl), and docosyl (behenyl).

Molecular weights of amphiphilic, cationic polymers according to the invention are preferably from 10,000 g/mol to 50,000,000 g/mol, especially from 50,000 g/mol to 5,000,000 g/mol, particularly preferably from 75,000 g/mol to 1,000,000 g/mol.

According to the invention, preferred agents contain the amphiphilic, cationic polymers (a) preferably in an amount of 0.1 wt. % to 20.0 wt. %, more preferably 0.2 wt. % to 10.0 wt. %, and particularly preferably 0.5 wt. % to 5.0 wt. %, based on total weight of the agent.

Properties of the agent according to the invention have proven to be particularly advantageous when the agent is packaged as an aerosol spray, aerosol foam, pump spray or pump foam. This preferred packaging form is described later in detail.

The following amphiphilic, cationic polymers (a) are preferably used in the agents when the amphiphilic, cationic polymers (a) corresponding to the above Formulas (I) to (IV) fulfill one or more of the following criteria—
- $R^1$ and $R^4$ are each a methyl group,
- $X^1$ is an NH group,
- $X^2$ is an NH group,
- $X^1$ and $X^2$ are an NH group,
- $A^1$ and $A^2$ are, independently of one another, ethane-1,2-diyl or propane-1,3-diyl,
- $R^2$, $R^3$, $R^5$ and $R^6$ are, independently of one another, methyl or ethyl (preferably methyl),
- $R^7$ is a ($C_{10}$ to $C_{24}$) alkyl group, particularly decyl (caprinyl), dodecyl (lauryl), tetradecyl (myristyl), hexadecyl (cetyl), octadecyl (stearyl), eicosyl (arachyl) or docosyl (behenyl).

Preferably, the structural unit of Formula (III) is chosen from at least one of the structural units according to Formula (III-1) to (III-8)—

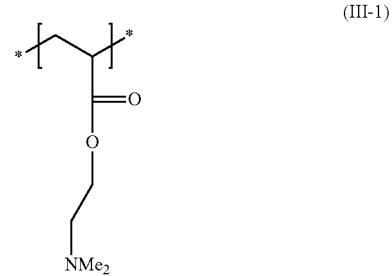

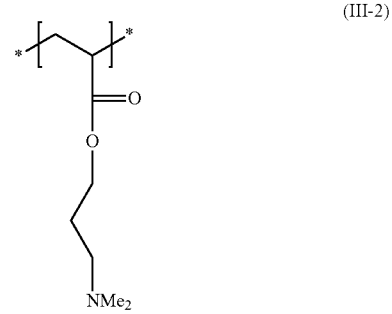

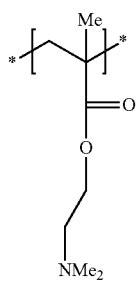
(III-3)

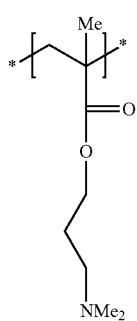
(III-4)

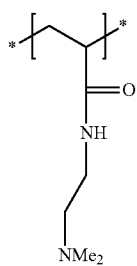
(III-5)

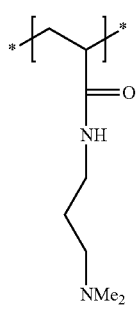
(III-6)

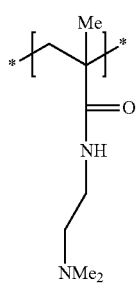
(III-7)

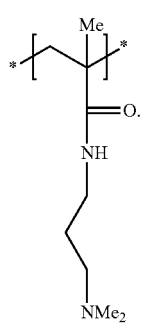
(III-8)

Moreover, it is particularly preferable to choose the structural unit according to Formula (III-7) and/or Formula (III-8) as the structural unit of Formula (III). According to the invention, the structural unit of Formula (III-8) is a quite particularly preferred structural unit.

Furthermore, the structural unit of Formula (IV) is preferably chosen from at least one structural unit according to Formulae (IV-1) to (IV-8)—

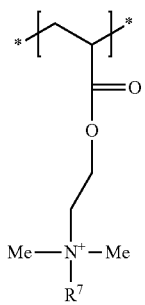
(IV-1)

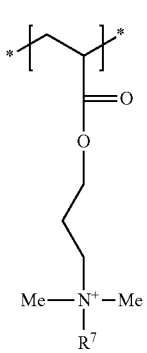
(IV-2)

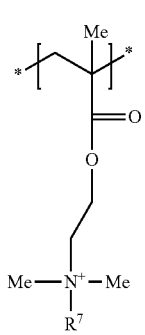
(IV-3)

(IV-4)
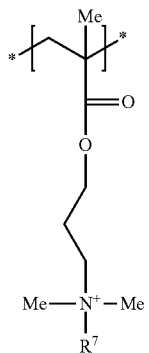

(IV-5)
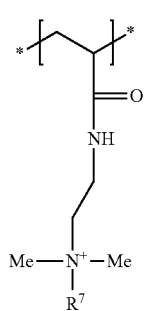

(IV-6)
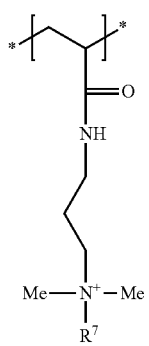

(IV-7)
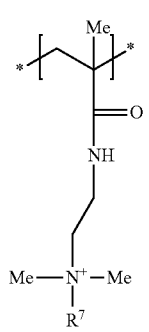

(IV-8)
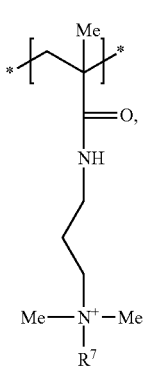

wherein each $R^7$ is a ($C_8$ to $C_{30}$) alkyl group.

The structural units of Formula (IV-7) and/or Formula (IV-8) are particularly preferred as the structural unit of Formula (IV), wherein each $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl). According to the invention, the structural unit of Formula (IV-8) is a quite particularly preferred structural unit of Formula (IV).

An amphiphilic, cationic polymer having at least one structural unit according to Formula (I), at least one structural unit according to Formula (II), at least one structural unit according to Formula (III-8), and at least one structural unit according to Formula (IV-8) is quite particularly preferably present in the agent according to the invention,

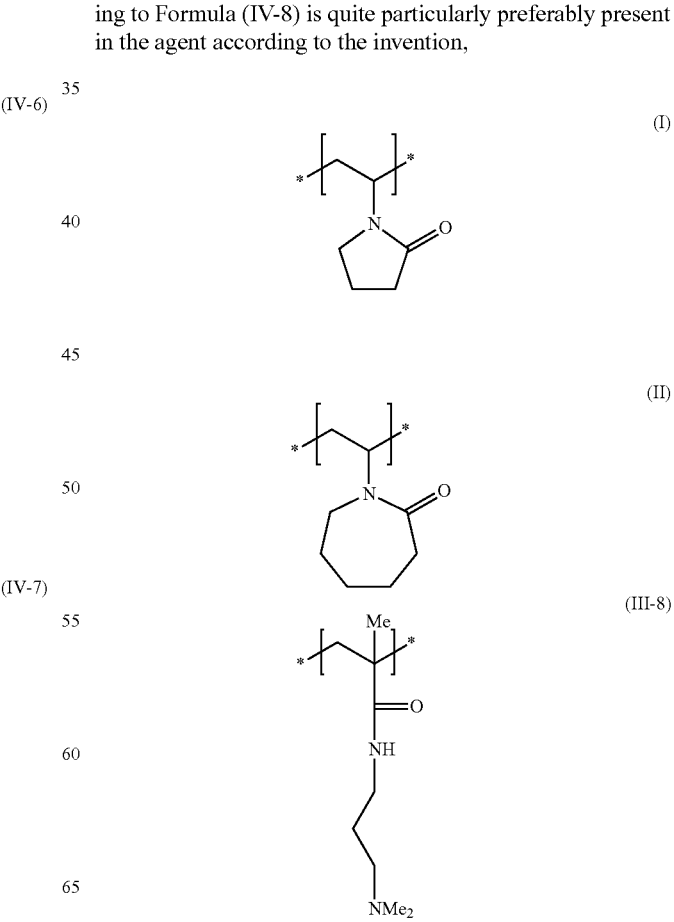

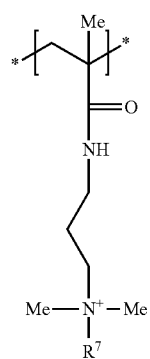

(IV-8)

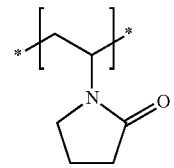

(I)

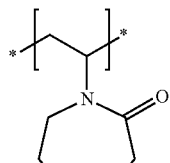

(II)

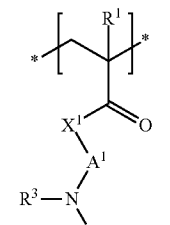

(III)

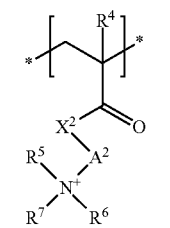

(IV)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl). A quite particularly preferred amphiphilic, cationic polymer according to the invention is the copolymer of N-vinyl pyrrolidone, N-vinyl caprolactam, N-(3-dimethylaminopropyl)methacrylamide and 3-(methacryloylamino)propyl-lauryl-dimethylammonium chloride (INCI name: Polyquaternium-69), marketed for example under the trade name AquaStyle® 300 (28-32 wt. % active substance in an ethanol-water mixture, molecular weight 350,000) by the ISP company.

In addition, the agent contains at least one film-forming cationic and/or setting polymer. These polymers differ from the amphiphilic, cationic polymers (a).

The additional film-forming cationic and/or setting cationic polymers preferably has at least one structural unit containing at least one permanently cationized nitrogen atom. "Permanently cationized nitrogen atoms" refers to those nitrogen atoms having a positive charge and thereby form a quaternary ammonium compound. Quaternary ammonium compounds are mostly produced by reacting tertiary amines with alkylating agents, such as methyl chloride, benzyl chloride, dimethyl sulfate, dodecyl bromide, as well as ethylene oxide. Depending on the tertiary amine, the following groups are particularly well known: alkylammonium compounds, alkenylammonium compounds, imidazolinium compounds and pyridinium compounds.

According to the invention, preferred agents contain film-forming, cationic and/or setting cationic polymers (b) preferably in an amount of 0.1 wt. % to 20.0 wt. %, more preferably 0.2 wt. % to 10.0 wt. %, and particularly preferably 0.5 wt. % to 5.0 wt. %, based on total weight of the agent.

According to the invention, cationic film-forming and/or cationic setting polymers can be chosen from cationic, quaternized cellulose derivatives.

In this embodiment, those agents are suitable that have, in a cosmetically acceptable carrier,
  (a) at least one amphiphilic, cationic polymer containing at least one structural unit of Formula (I), at least one structural unit of Formula (II), at least one structural unit of Formula (III) and at least one structural unit of Formula (IV), wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional film-forming cationic and/or setting cationic polymer, selected from the group of the cationic, quaternized cellulose derivatives, and (c) at least one film-forming non-ionic and/or setting non-ionic polymer.

Accordingly, in the context of this embodiment, those agents are suitable that have, in a cosmetically acceptable carrier,—
  (a) at least one amphiphilic, cationic polymer containing at least one structural unit of Formula (I), at least one structural unit of Formula (II), at least one structural unit of Formula (III-8) and at least one structural unit of Formula (IV-8),

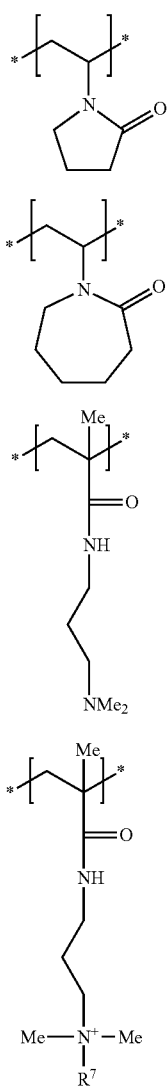

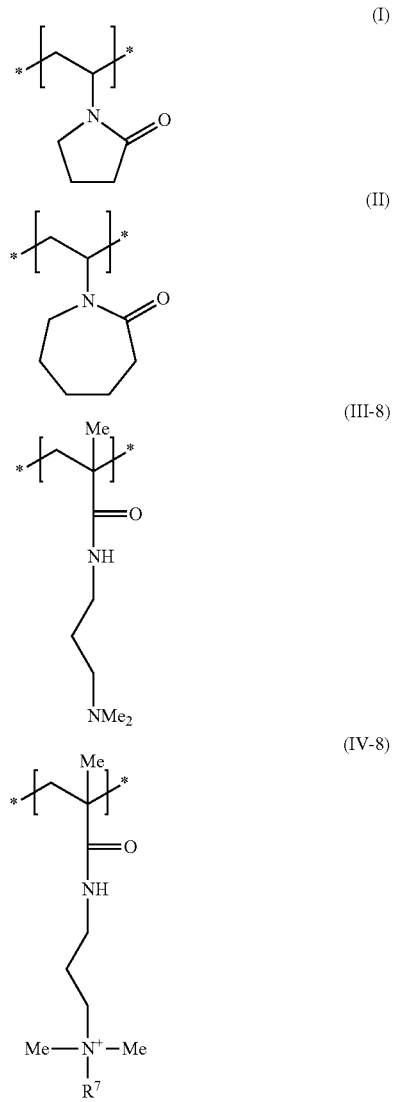

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives, and (c) at least one film-forming non-ionic and/or setting non-ionic polymer.

In general, those cationic, quaternized celluloses having more than one permanent cationic charge in a side chain have proven to be advantageous according to the invention. Among the cationic cellulose derivatives that are to be highlighted are those produced from the reaction of hydroxyethyl cellulose with a dimethyldiallylammonium reactant (especially dimethyldiallylammonium chloride) optionally in the presence of further reactants. Among these cationic celluloses that are particularly suitable are those with the INCI name Polyquaternium-4, marketed, for example, by the National Starch Company under the trade names Celquat® H 100, Celquat® L 200.

Consequently, in the context of this embodiment, agents according to the invention are suitable that have, in a cosmetically acceptable carrier, (a) at least one amphiphilic, cationic polymer containing at least one structural unit of Formula (I), at least one structural unit of Formula (II), at least one structural unit of Formula (III-8) and at least one structural unit of Formula (IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives produced from the reaction of hydroxyethyl cellulose with a dimethyldiallylammonium reactant (especially dimethyldiallylammonium chloride), optionally in the presence of further reactants, and (c) at least one film-forming non-ionic and/or setting non-ionic polymer.

In the context of these abovementioned embodiments, the previously cited preferred embodiments of the amphiphilic, cationic polymer (a) are suitable (see above). Similarly, all the previously mentioned preferred quantitative data regarding polymer components (a) and (b) of the agent are also well suited mutatis mutandis for these embodiments.

Further, cationic film-forming and/or cationic setting polymers having at least one structural unit of Formula (I), at least one structural unit of Formula (VI), and optionally at least one structural unit of Formula (V) are suitable

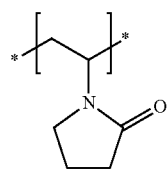
(I)

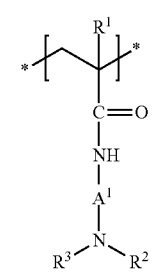
(V)

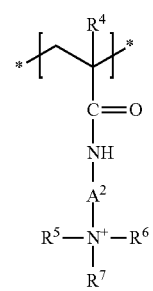
(VI)

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, and $R^7$ is a ($C_8$ to $C_{30}$) alkyl group.

To compensate for the positive charge of monomer (VI), all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, and triflate.

Accordingly, in the context of the present invention, those agents are suitable that have, in a cosmetically acceptable carrier, (a) at least one amphiphilic, cationic polymer containing at least one structural unit of Formula (I), at least one structural unit of Formula (II), at least one structural unit of Formula (III), and at least one structural unit of Formula (IV),

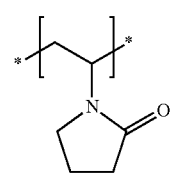
(I)

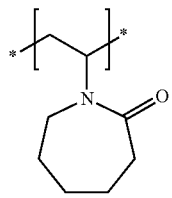
(II)

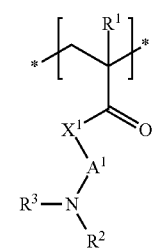
(III)

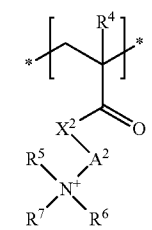
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional cationic film-forming and/or cationic setting polymer containing at least one structural unit of Formula (I), at least one structural unit of Formula (VI), and optionally at least one structural unit of Formula (V)

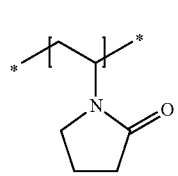
(I)

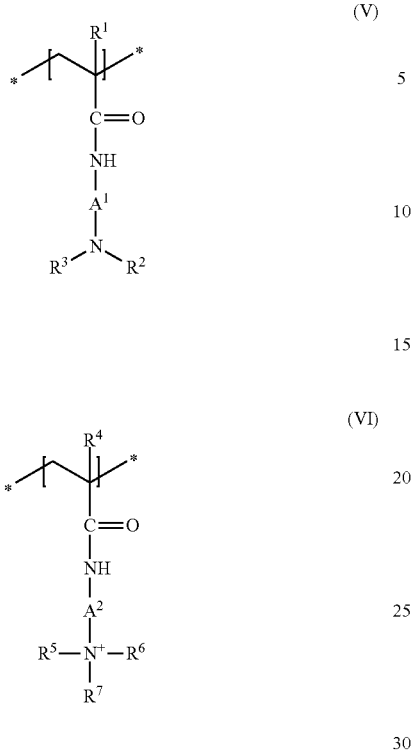

(V)

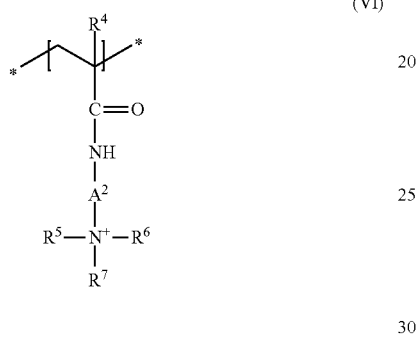

(VI)

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (c) at least one film-forming non-ionic and/or setting non-ionic polymer.

In addition, in the context of this embodiment, those agents are suitable that have, in a cosmetically acceptable carrier,—

(a) at least one amphiphilic, cationic polymer containing at least one structural unit of Formula (I), at least one structural unit of Formula (II), at least one structural unit of Formula (III-8), and at least one structural unit of Formula (IV-8)

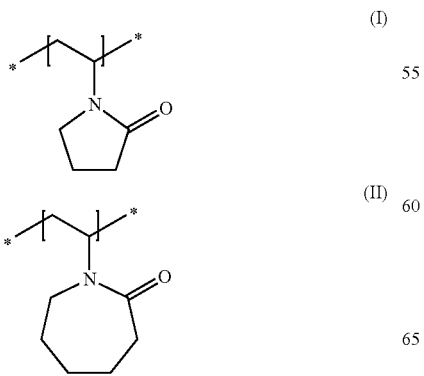

(I)

(II)

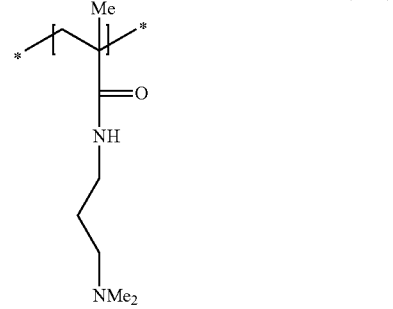

(III-8)

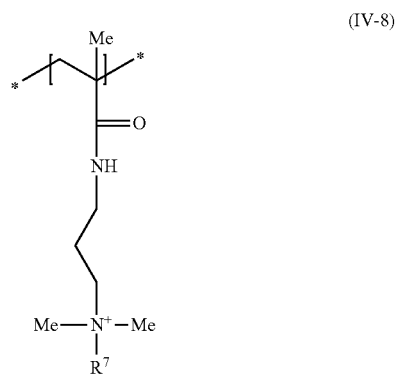

(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional cationic film-forming and/or cationic setting polymer containing at least one structural unit of Formula (I), at least one structural unit of Formula (VI), and optionally at least one structural unit of Formula (V)

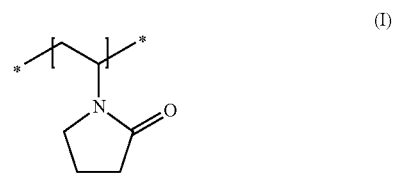

(I)

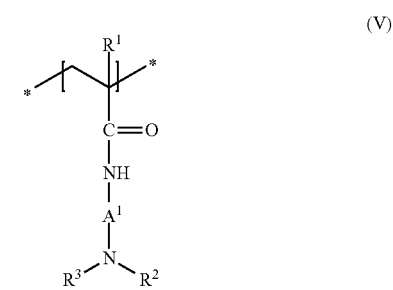

(V)

-continued

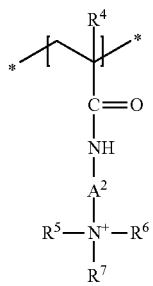
(VI)

wherein

R[1] and R[4] are, independently of one another, a hydrogen atom or a methyl group, A[1] and A[2] are, independently of one another, an ethane-1,2-diyl, propane-1,3-diyl or butane-1,4-diyl group, R[2], R[3], R[5] and R[6] are, independently of one another, a ($C_1$ to $C_4$) alkyl group, R[7] is a ($C_8$ to $C_{30}$) alkyl group, and (c) at least one film-forming non-ionic and/or setting non-ionic polymer.

To compensate for the positive charge of monomer (VI), the above relevant statement applies.

Exemplary suitable compounds are— copolymers of dimethylaminoethyl methacrylate, quaternized with diethyl sulfate, with vinyl pyrrolidone having the INCI name Polyquaternium-11, commercially available under the trade names Gafquat® 440, Gafquat® 734, Gafquat® 755 (each from ISP) and Luviquat PQ 11 PN (BASF SE), and copolymers of methacryloyl aminopropyllauryldimethylammonium chloride with vinyl pyrrolidone and dimethylaminopropylmethacrylamide with the INCI name Polyquaternium-55, commercially available under the trade names, Styleze® W-10, Styleze® W-20 (ISP).

In the context of this embodiment, the previously cited preferred embodiments of the amphiphilic, cationic polymer (a) are preferred (see above). Similarly, all previously mentioned quantitative data regarding polymer components (a) and (b) of the agent are also preferred mutatis mutandis for these embodiments.

Additionally, in the context of the invention, those cationic film-forming and/or cationic setting copolymers (b) having at least one structural element of Formula (M1) serve as the particularly preferred usable film-forming and/or setting polymers chosen from cationic polymers having at least one structural unit possessing a permanently cationized nitrogen atom

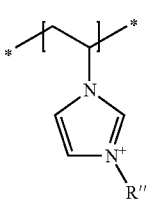
(M1)

wherein R" is a ($C_1$ to $C_4$) alkyl group, preferably a methyl group, and additionally possessing another cationic and/or non-ionic structural element.

Accordingly, those agents are particularly preferred that have, in a cosmetically acceptable carrier,—

(a) at least one amphiphilic, cationic polymer containing at least one structural unit of Formula (I), at least one structural unit of Formula (II), at least one structural unit of Formula (III), and at least one structural unit of Formula (IV),

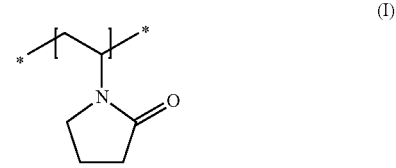
(I)

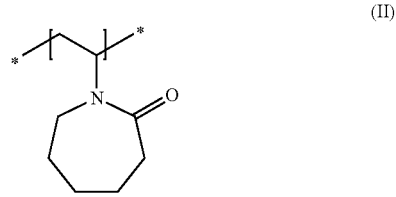
(II)

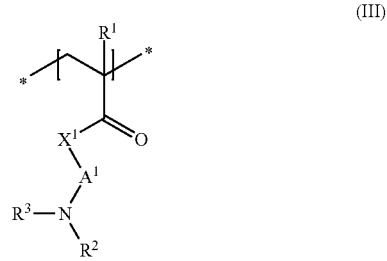
(III)

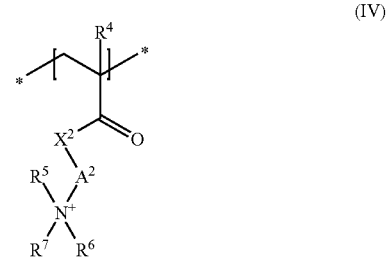
(IV)

wherein

R[1] and R[4] are, independently of one another, a hydrogen atom or a methyl group, X[1] and X[2] are, independently of one another, an oxygen atom or an NH group, A[1] and A[2] are, independently of one another, an ethane-1,2-diyl, propane-1,3-diyl or butane-1,4-diyl group, R[2], R[3], R[5] and R[6] are, independently of one another, a ($C_1$ to $C_4$) alkyl group, R[7] is a ($C_8$ to $C_{30}$) alkyl group, and (b) at least one additional cationic film-forming and/or cationic setting polymer havin at least one structural element of Formula (M1) as the at least one structural unit having a permanently cationized nitrogen atom

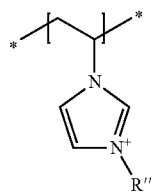
(M1)

wherein R" is a (C₁ to C₄) alkyl group, particularly a methyl group, and additionally possessing at least one other cationic and/or non-ionic structural element, and (c) at least one film-forming non-ionic and/or setting non-ionic polymer.

To compensate for the positive polymer charge of component (b), all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, and triflate.

In the context of this embodiment, those agents are particularly preferred that have, in a cosmetically acceptable carrier, (a) at least one amphiphilic, cationic polymer containing at least one structural unit of Formula (I), at least one structural unit of Formula (II), at least one structural unit of Formula (III-8), and at least one structural unit of Formula (IV-8)

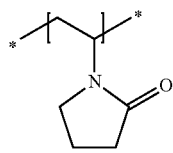
(I)

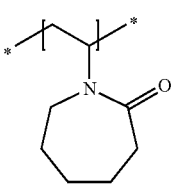
(II)

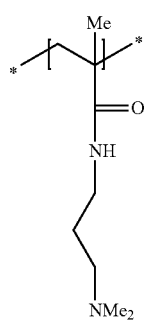
(III-8)

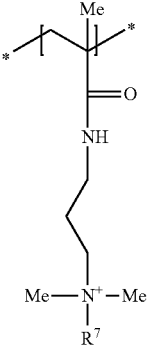
(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1)

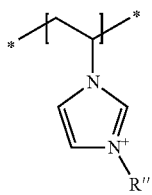
(M1)

wherein R" is a (C₁ to C₄) alkyl group, particularly a methyl group, and additionally possesses at least one other cationic and/or non-ionic structural element, and (c) at least one film-forming non-ionic and/or setting non-ionic polymer.

In particular, the polymer with the INCI name Polyquaternium 69 is particularly preferred as the amphiphilic cationic polymer (a) (see above).

To compensate for the positive polymer charge of component (b), the above relevant statement applies.

It is preferred when, in addition to the amphiphilic cationic polymer (a), at least one copolymer (b1) is present in the agent that, in addition to a structural element of Formula (M1), further contains a structural element of Formula (I) as the cationic film-forming and/or cationic setting polymer (b) of this embodiment—

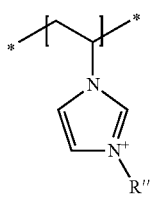
(M1)

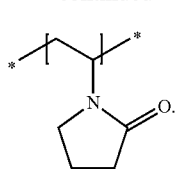
(I)

wherein R" is a ($C_1$ to $C_4$) alkyl group, particularly a methyl group.

To compensate for the positive polymer charge of copolymer (b1), all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Quite particularly preferred cationic film-forming and/or cationic setting polymers as copolymers (b1) contain 10 to 30 mol %, preferably 15 to 25 mol % and particularly 20 mol % of structural units according to Formula (M1) and 70 to 90 mol %, preferably 75 to 85 mol % and particularly 80 mol % of structural units according to Formula (I).

In this regard it is particularly preferred when copolymers (b1) contain, in addition to polymer units resulting from the incorporation of those structural units according to Formulae (M1) and (I) into the copolymer, maximum 5 wt. %, preferably maximum 1 wt. % of polymer units that trace back to the incorporation of other monomers. Copolymers (b1) are preferably exclusively formed from structural units of Formula (M1) with R"=methyl and (I) and can be described by the general Formula (Poly1)

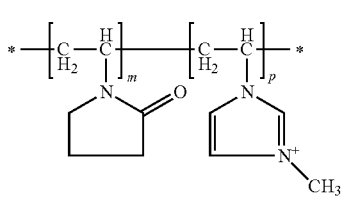
(Poly1)

wherein indices m and p vary according to the molecular mass of the polymer and do not necessarily portray block copolymers. In fact, structural units of Formula (M1) and Formula (I) can be statistically distributed in the molecule.

If a chloride ion is used to compensate for the positive charge of the polymer of Formula (Poly1), then these N-methyl vinylimidazole/vinyl pyrrolidone copolymers are named according to INCI nomenclature as Polyquaternium-16 and are available from, for example, BASF under the trade names Luviquat® Style, Luviquat® FC 370, Luviquat® FC 550, Luviquat® FC 905 and Luviquat® HM 552.

If a methosulfate ion is used to compensate for the positive charge of the polymer of Formula (Poly1), then these N-methyl vinylimidazole/vinyl pyrrolidone copolymers are named according to INCI nomenclature as Polyquaternium-44 and are available from for example BASF under the trade name Luviquat® UltraCare.

Particularly preferred agents contain a copolymer (b1), especially Formula (Poly1), having molecular masses within a defined range. Here, agents are preferred wherein the molecular mass of copolymer (b1) is from 50 to 400 kDa, preferably from 100 to 300 kDa, more preferably from 150 to 250 kDa, and particularly from 190 to 210 kDa.

In addition to copolymer(s) (b1) or instead of it or them, the agents can also comprise copolymers (b2) that, starting from copolymer (b1), possess as additional structural units structural units of Formula (II)

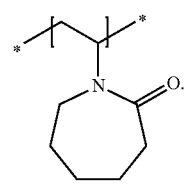
(II)

Further particularly preferred agents according to the invention are accordingly those having as the cationic film-forming and/or cationic setting polymer (b) at least one copolymer (b2) having at least one structural unit according to Formula (M1-a) and at least one structural unit according to Formula (I) and at least one structural unit according to Formula (II)

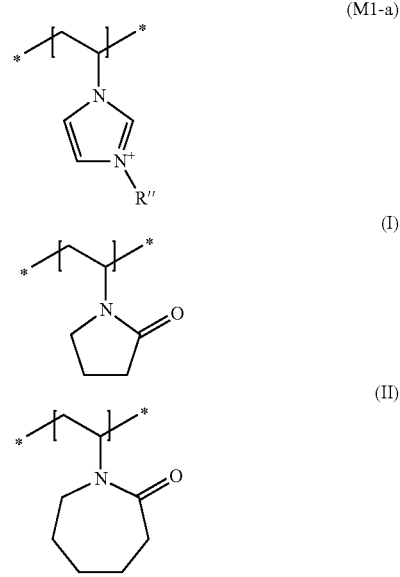

Also, it is particularly preferred when copolymers (b2) contain, in addition to polymer units resulting from the incorporation of structural units according to Formulae (M1-a), (I) and (II) into the copolymer, a maximum of 5 wt. %, preferably a maximum of 1 wt. % of polymer units that trace back to the incorporation of other monomers. Copolymers (b2) are preferably exclusively formed from structural units of Formulae (M1-a), (I) and (II) and can be described by the general Formula (Poly2)

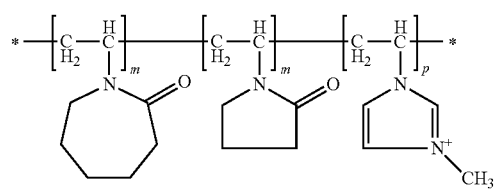
(Poly2)

wherein indices m, n and p vary according to the molecular mass of the polymer and do not necessarily portray block copolymers. In fact, structural units of the cited Formulae can be statistically distributed in the molecule.

To compensate for the positive polymer charge of component (b2), all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

If a methosulfate ion is used to compensate for the positive charge of the polymer of Formula (Poly2), then these N-methyl vinylimidazole/vinyl pyrrolidone/vinyl caprolactam copolymers, named according to INCI nomenclature as Polyquaternium-46 and available from, for example, BASF under the trade name Luviquat® Hold.

Quite particularly preferred copolymers (b2) contain 1 to 20 mol %, preferably 5 to 15 mol %, and particularly 10 mol % of structural units according to Formula (M1-a), 30 to 50 mol %, preferably 35 to 45 mol % and particularly 40 mol % of structural units according to Formula (I), and 40 to 60 mol %, preferably 45 to 55 mol % and particularly 60 mol % of structural units according to Formula (II).

Particularly preferred agents have a copolymer (b2) that has molecular masses within a defined range. Here, agents are preferred in which the molecular mass of copolymer (b2) is from 100 to 1000 kDa, preferably from 250 to 900 kDa, more preferably from 500 to 850 kDa and particularly from 650 to 710 kDa.

In addition to copolymer(s) (b1) and/or (b2) or in its or their place, the agents can also include copolymers (b3) as the film-forming cationic and/or setting cationic polymer (b) having as structural units the structural units of Formulae (M1-a) and (I), as well as additional structural units from the group of vinyl imidazole units and further structural units from the group of acrylamide and/or methacrylamide units.

Further particularly preferred agents according to the invention contain as the cationic film-forming and/or cationic setting polymer (b) at least one copolymer (b3) having at least one structural unit according to Formula (M1-a), at least one structural unit according to Formula (I), at least one structural unit according to Formula (VII), and at least one structural unit according to Formula (VIII)

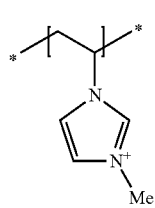
(M1-a)

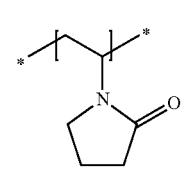
(I)

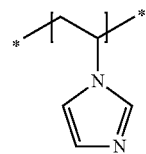
(VII)

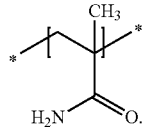
(VIII)

Also, it is particularly preferred when copolymers (b3) have, in addition to polymer units resulting from the incorporation of the cited structural units according to Formulae (M1-a), (I), (VII) and (VIII) into the copolymer, a maximum of 5 wt. %, preferably a maximum of 1 wt. % of polymer units that trace back to the incorporation of other monomers. Copolymers (b3) are preferably exclusively formed from structural units of Formula (M1-a), (I), (VII) and (VIII) and can be described by the general Formula (Poly3)

(Poly3)

wherein indices m, n, o and p vary according to the molecular mass of the polymer and do not necessarily portray block copolymers. In fact, structural units of Formula (M1-a), (I), (VII) and (VIII) can be statistically distributed in the molecule.

To compensate for the positive polymer charge of component (b2), all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

If a methosulfate ion is used to compensate for the positive charge of the polymer of Formula (Poly3), then these N-methyl vinylimidazole/vinyl pyrrolidone/vinyl imidazole/methacrylamide copolymers are named according to INCI nomenclature as Polyquaternium-68 and are available from for example BASF under the trade name Luviquat® Supreme.

Quite particularly preferred copolymers (b3) contain 1 to 12 mol %, preferably 3 to 9 mol %, and particularly 6 mol % of structural units according to Formula (M1-a); 45 to 65 mol %, preferably 50 to 60 mol % and particularly 55 mol % of structural units according to Formula (I); 1 to 20 mol %, preferably 5 to 15 mol % and particularly 10 mol % of structural units according to Formula (VII); and 20 to 40 mol %, preferably 25 to 35 mol % and particularly 29 mol % of structural units according to Formula (VIII).

Particularly preferred inventive agents contain a copolymer (b3) having molecular masses within a defined range. Here, inventive agents are preferred wherein the molecular mass of copolymer (b3) is from 100 to 500 kDa, preferably from 150 to 400 kDa, more preferably from 250 to 350 kDa and particularly from 290 to 310 kDa.

Preferred additional film-forming cationic and/or setting polymers chosen from cationic polymers (b) with at least one structural element of the above Formula (M1) include:

- vinyl pyrrolidone/1-vinyl-3-methyl-1H-hnidazolium chloride copolymers (such as for example that with the INCI name Polyquaternium-16 sold under the trade names Luviquat® Style, Luviquat® FC 370, Luviquat® FC 550, Luviquat® FC 905 and Luviquat® HM 552 (BASF SE)),
- vinyl pyrrolidone/1-vinyl-3-methyl-1H-imidazolium methyl sulfate copolymers (such as for example that with the INCI name Polyquaternium-44 sold under the trade name Luviquat® Care (BASF SE)),
- vinyl pyrrolidone/vinyl caprolactam/1-vinyl-3-methyl-1H-imidazolium terpolymer (such as for example that with the INCI name Polyquaternium-46 sold under the trade names Luviquat® Care or Luviquat® Hold (BASF SE)), and
- vinyl pyrrolidone/methacrylamide/vinyl imidazole/1-vinyl-3-methyl-1H-imidazolium methyl sulfate copolymer (such as for example that with the INCI name Polyquaternium-68 sold under the trade name Luviquat® Supreme (BASF SE)), as well as mixtures of these polymers.

In the context of this embodiment, the previously cited preferred embodiments of the amphiphilic, cationic polymer (a) are preferred (see above). Similarly, all previously mentioned quantitative data regarding polymer components (a) and (b) of the agent are also preferred mutatis mutandis for these embodiments.

In addition, the agent according to the invention contains at least one film-forming non-ionic and/or setting non-ionic polymer (c). According to the invention, a non-ionic polymer refers to a polymer that, in a protic solvent under standard conditions, carries essentially no structural units containing cationic or anionic groups that have to be compensated by counter ions in order to maintain electroneutrality. Cationic groups include quaternized ammonium groups but no protonated amines. Anionic groups include carboxylic and sulfonic acid groups.

The agent preferably contains non-ionic, film-forming and/or non-ionic, setting polymers (c) in an amount of 0.1 wt. % to 20.0 wt. %, more preferably 0.2 wt. % to 15.0 wt. %, quite preferably 0.5 wt. % to 10.0 wt. %, based on total weight of the agent according to the invention.

Film-forming non-ionic and/or setting non-ionic polymers (c) are preferably chosen from at least one polymer of the group of homopolymers and non-ionic copolymers of N-vinyl pyrrolidone.

Suitable polyvinyl pyrrolidones include commercial products such as Luviskol® K 90 or Luviskol® K 85 from BASF SE.

Agents having as the film-forming non-ionic and/or setting non-ionic polymers (c) at least one polymer chosen from—
- polyvinyl pyrrolidone,
- copolymers of N-vinyl pyrrolidone and vinyl esters of carboxylic acids containing 2 to 8 carbon atoms, especially N-vinyl pyrrolidone and vinyl acetate,
- copolymers of N-vinyl pyrrolidone and N-vinylimidazole and methacrylamide,
- copolymers of N-vinyl pyrrolidone and N-vinylimidazole and acrylamide,
- copolymers of N-vinyl pyrrolidone with N,N-di($C_1$ to $C_4$) alkylamino ($C_2$ to $C_4$) alkylacrylamide, are inventively quite particularly preferred.

In the context of this embodiment, those agents are quite particularly preferred that have, in a cosmetically acceptable carrier, (a) at least one amphiphilic, cationic polymer containing at least one structural unit of Formula (I), at least one structural unit of Formula (II), at least one structural unit of Formula (III-8), and at least one structural unit of Formula (IV-8),

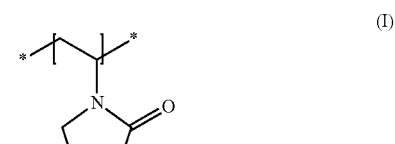

(I)

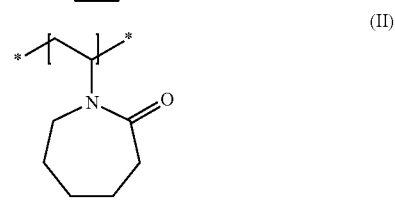

(II)

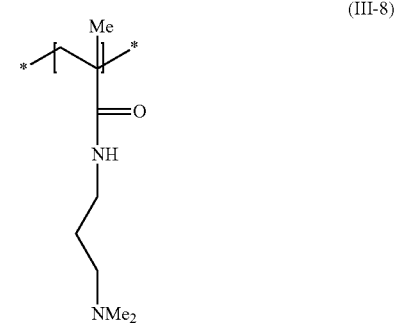

(III-8)

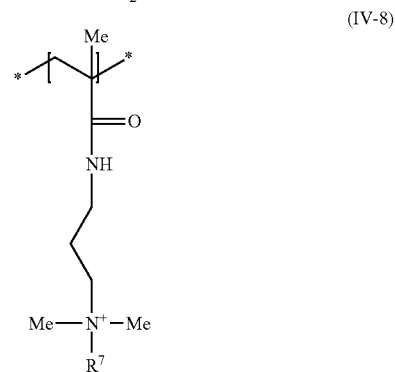

(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl); and (b) at least one additional film-forming cationic and/or setting cationic polymer; and (c) polyvinyl pyrrolidone.

In the context of this embodiment, those agents are quite particularly preferred that have, in a cosmetically acceptable carrier, (a) at least one amphiphilic, cationic polymer containing at least one structural unit of Formula (I), at least one structural unit of Formula (II), at least one structural unit of Formula (III-8), and at least one structural unit of Formula (IV-8),

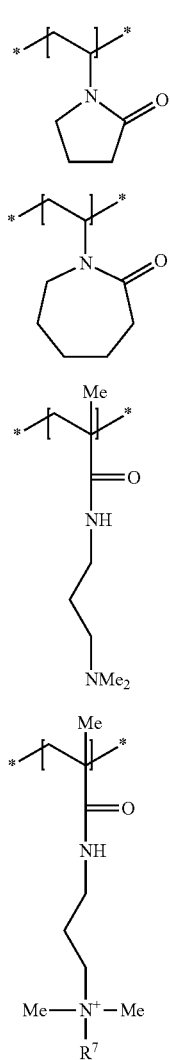

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer, and (c) a copolymer manufactured from monomers N-vinyl pyrrolidone and vinyl acetate—particularly from no additional monomers.

In this regard it is again preferred when the molar ratio of the comprised structural units of monomer N-vinyl pyrrolidone to the comprised structural units of monomer vinyl acetate of the polymer is in the range of 20 to 80 to 80 to 20, particularly 30 to 70 to 60 to 40.

Suitable copolymers of vinyl pyrrolidone and vinyl acetate are available, for example, under the trade names Luviskol® VA 37, Luviskol® VA 55, Luviskol® VA 64 and Luviskol® VA 73 from BASF SE.

Further preferred agents according to the invention contain as the non-ionic film-forming and/or non-ionic setting polymer (c) at least one copolymer (c1) having at least another structural unit according to Formula (I), at least one structural unit according to Formula (VII), and at least one structural unit according to Formula (VIII)

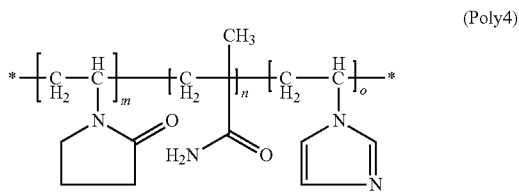

Also, it is particularly preferred when these copolymers comprise, in addition to polymer units resulting from the incorporation of the cited structural units according to Formula (M1-a), (I), (VII) and (VIII) into the copolymer, a maximum of 5 wt. %, preferably a maximum of 1 wt. % of polymer units that trace back to the incorporation of other monomers. Copolymers (b3) are preferably exclusively formed from structural units of Formula (M1-a), (I), (VII) and (VIII) and can be described by the general Formula (Poly4)

(Poly4)

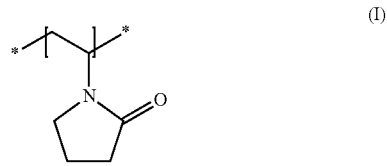

wherein indices m, n, o and p vary according to the molecular mass of the polymer and do not necessarily portray block copolymers. In fact, structural units of Formula (I), (VII) and (VIII) can be statistically distributed in the molecule.

In the context of this embodiment, those agents are quite particularly preferred that have, in a cosmetically acceptable carrier,—

(a) at least one amphiphilic, cationic polymer containing at least one structural unit of Formula (I), at least one structural unit of Formula (II), at least one structural unit of Formula (III-8), and at least one structural unit of Formula (IV-8), -continued

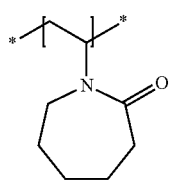
(II)

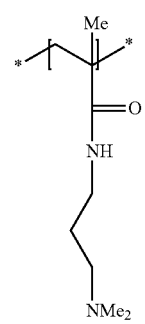
(III-8)

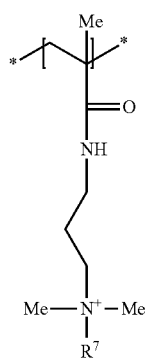
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer, and (c) at least one non-ionic film-forming and/or non-ionic setting polymer containing structural units according to Formula (I), structural units according to Formula (VII), and structural units according to Formula (VIII)

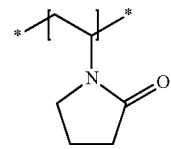
(I)

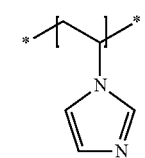
(VII)

-continued

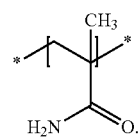
(VIII)

A particularly preferred polymer is chosen from polymers of the INCI name VP/Methacrylamide/Vinyl Imidazole Copolymer, available, for example, from BASF SE under the trade name Luviset® Clear.

According to the invention, it is preferable to use agents having at least one non-ionic film-forming and/or non-ionic setting polymer (c) containing at least one structural unit of Formula (I) and at least one structural unit of Formula (III)

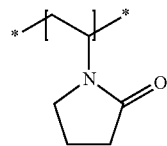
(I)

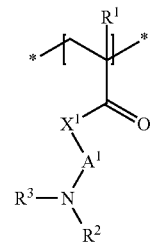
(III)

wherein $R^1$ is a hydrogen atom or a methyl group, $X^1$ is an oxygen atom or an NH group, $A^1$ is an ethane-1,2-diyl, propane-1,3-diyl or butane-1,4-diyl group, $R^2$ and $R^3$ are, independently of one another, a ($C_1$ to $C_4$) alkyl group.

In the context of this embodiment, those agents are quite particularly preferred that have, in a cosmetically acceptable carrier, (a) at least one amphiphilic, cationic polymer containing at least one structural unit of Formula (I), at least one structural unit of Formula (II), at least one structural unit of Formula (III-8), and at least one structural unit of Formula (IV-8),

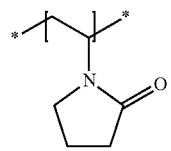
(I)

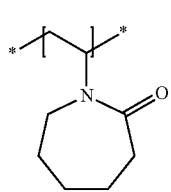
(II)

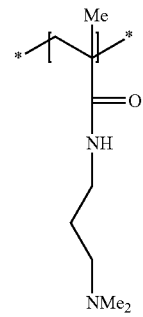
(III-8)

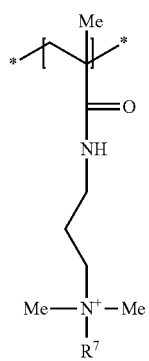
(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and
(b) at least one additional film-forming cationic and/or setting cationic polymer, and
(c) at least one non-ionic film-forming and/or non-ionic setting polymer containing at least one structural unit of Formula (I) and at least one structural unit of Formula (III)

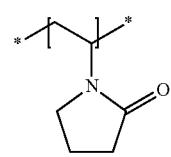
(I)

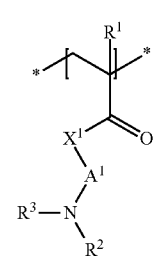
(III)

wherein
$R^1$ is a hydrogen atom or a methyl group,
$X^1$ is an oxygen atom or an NH group,
$A^1$ is an ethane-1,2-diyl, propane-1,3-diyl or butane-1,4-diyl group,
$R^2$ and $R^3$ are, independently of one another, a ($C_1$ to $C_4$) alkyl group.

In this regard it is particularly preferred when the non-ionic film-forming and/or non-ionic setting polymer is chosen from at least one polymer that fulfils at least one or more of the following criteria:
$R^1$ is a methyl group,
$X^1$ is an NH group,
$A^1$ is ethane-1,2-diyl or propane-1,3-diyl,
$R^2$ and $R^3$ are, independently of one another, methyl or ethyl, (preferably methyl).

Non-ionic film-forming and/or non-ionic setting polymers of this embodiment particularly preferably concerns at least one polymer having at least one structural unit of Formula (I) and at least one structural unit of Formula (III-8),

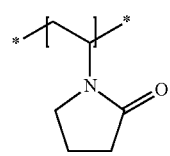
(I)

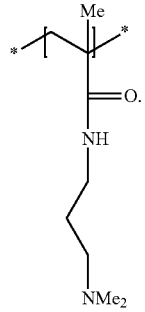
(III-8)

A particularly preferred non-ionic film-forming and/or non-ionic setting polymer of this embodiment is a copolymer of N-vinyl pyrrolidone and N,N-dimethyl aminopropyl methacrylamide that is sold, for example, with the INCI name VP/DMAPA Acrylates Copolymer, for example, under the trade name Styleze® CC 10 by ISP.

In the context of all these embodiments, the previously cited preferred embodiments of the amphiphilic, cationic polymer (a) are preferred (see above). Similarly, all previously mentioned quantitative data regarding polymer components (a) and (b) and (c) of the agent are also preferred mutatis mutandis for these embodiments.

Those agents are particularly preferred that have, in a cosmetically acceptable carrier,
(a) at least one amphiphilic, cationic polymer containing at least one structural unit of Formula (I), at least one structural unit of Formula (II), at least one structural unit of Formula (III), and at least one structural unit of Formula (IV),

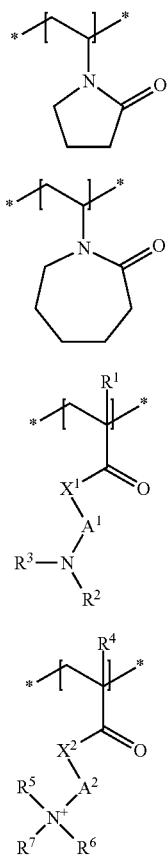

(I)

(II)

(III)

(IV)

wherein
R¹ and R⁴ are, independently of one another, a hydrogen atom or a methyl group,
X¹ and X² are, independently of one another, an oxygen atom or an NH group,
A¹ and A² are, independently of one another, an ethane-1,2-diyl, propane-1,3-diyl or butane-1,4-diyl group,
R², R³, R⁵ and R⁶ are, independently of one another, a ($C_1$ to $C_4$) alkyl group,
R⁷ is a ($C_8$ to $C_{30}$) alkyl group, and (b) at least one additional film-forming cationic and/or setting cationic polymer chosen from cationic, quaternized cellulose derivatives, and (c) polyvinyl pyrrolidone.

Those agents are particularly preferred that have, in a cosmetically acceptable carrier, (a) at least one amphiphilic, cationic polymer containing at least one structural unit of Formula (I), at least one structural unit of Formula (II), at least one structural unit of Formula (III), and at least one structural unit of Formula (IV),

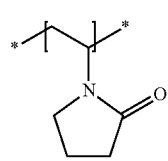

(I)

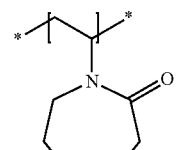

(II)

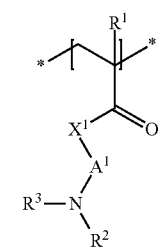

(III)

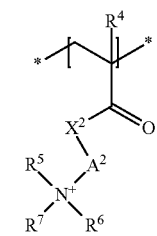

(IV)

wherein
R¹ and R⁴ are, independently of one another, a hydrogen atom or a methyl group,
X¹ and X² are, independently of one another, an oxygen atom or an NH group,
A¹ and A² are, independently of one another, an ethane-1,2-diyl, propane-1,3-diyl or butane-1,4-diyl group,
R², R³, R⁵ and R⁶ are, independently of one another, a ($C_1$ to $C_4$) alkyl group,
R⁷ is a ($C_8$ to $C_{30}$) alkyl group, and (b) at least one additional film-forming cationic and/or setting cationic polymer chosen from cationic, quaternized cellulose derivatives, and (c) a copolymer manufactured from the monomers N-vinyl pyrrolidone and vinyl acetate—particularly from no additional monomers.

Those agents are particularly preferred that have, in a cosmetically acceptable carrier, (a) at least one amphiphilic, cationic polymer containing at least one structural unit of Formula (I), at least one structural unit of Formula (II), at least one structural unit of Formula (III), and at least one structural unit of Formula (IV),

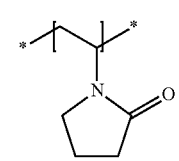

(I)

-continued

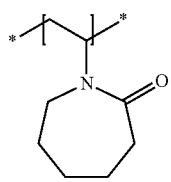
(II)

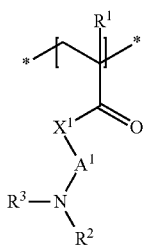
(III)

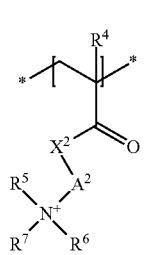
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional film-forming cationic and/or setting cationic polymer chosen from cationic, quaternized cellulose derivatives, and (c) at least one non-ionic film-forming and/or non-ionic setting polymer having structural units according to Formula (I), structural units according to Formula (VII), and structural units according to Formula (VIII)

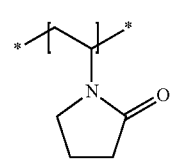
(I)

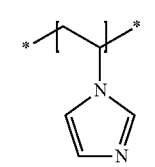
(VII)

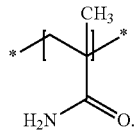
(VIII)

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

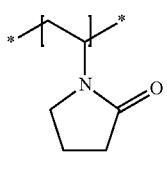
(I)

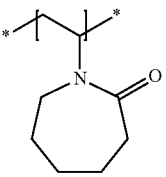
(II)

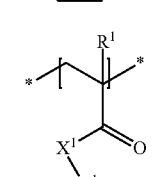
(III)

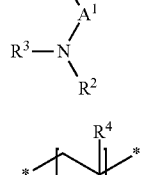
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional film-forming cationic and/or setting cationic polymer chosen from cationic, quaternized cellulose derivatives, and (c) at least one non-ionic film-forming and/or non-ionic setting polymer having at least one structural unit of Formula (I) and at least one structural unit of Formula (III)

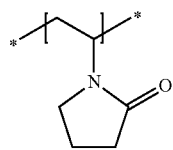
(I)

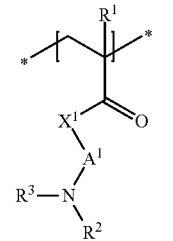
(III)

wherein $R^1$ is a hydrogen atom or a methyl group, $X^1$ is an oxygen atom or an NH group, $A^1$ is an ethane-1,2-diyl, propane-1,3-diyl or butane-1,4-diyl group, and $R^2$ and $R^3$ are, independently of one another, a ($C^1$ to $C^4$) alkyl group.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III-8), and at least one structural unit of Formula (IV),

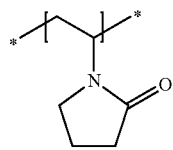
(I)

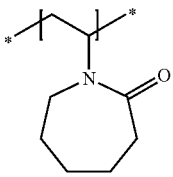
(II)

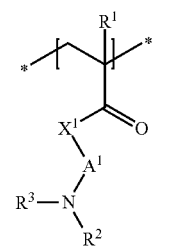
(III)

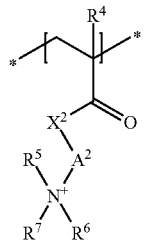
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional cationic film-forming and/or cationic setting polymer having at least one structural unit of Formula (I), at least one structural unit of Formula (VI), and optionally at least one structural unit of Formula (V)

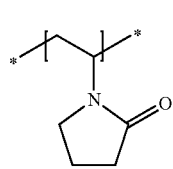
(I)

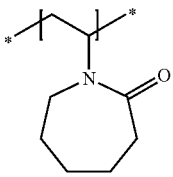
(V)

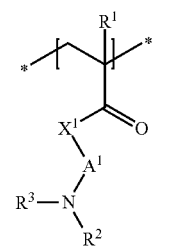
(VI)

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (c) polyvinyl pyrrolidone.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III-8), and at least one structural unit of Formula (IV),

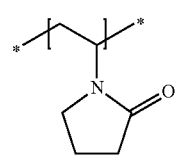
(I)

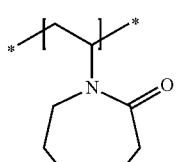
(II)

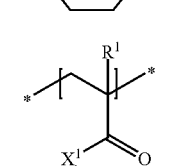
(III)

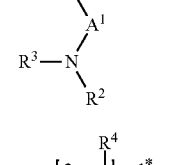
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional cationic film-forming and/or cationic setting polymer having at least one structural unit of Formula (I), at least one structural unit of Formula (VI), and optionally at least one structural unit of Formula (V)

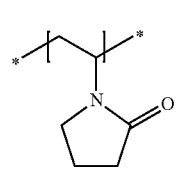
(I)

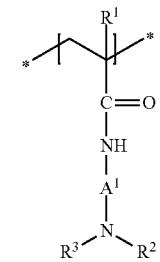
(V)

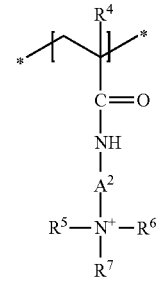
(VI)

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (c) a copolymer manufactured from monomers N-vinyl pyrrolidone and vinyl acetate—particularly from no additional monomers.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

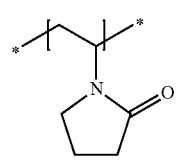
(I)

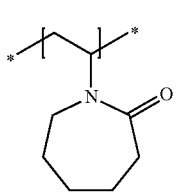
(II)

(III)

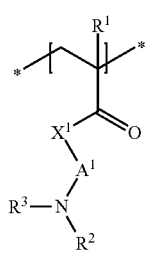

(IV)

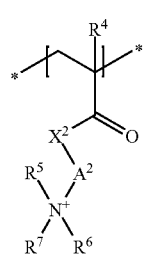

wherein

R¹ and R⁴ are, independently of one another, a hydrogen atom or a methyl group,

X¹ and X² are, independently of one another, an oxygen atom or an NH group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_8$ to $C_{30}$) alkyl group, and (b) at least one additional cationic film-forming and/or cationic setting polymer having at least one structural unit of Formula (I), at least one structural unit of Formula (VI), and optionally at least one structural unit of Formula (V)

(I)

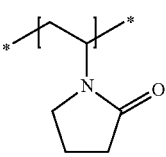

(V)

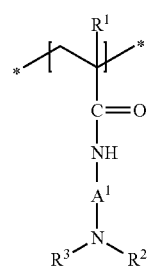

(VI)

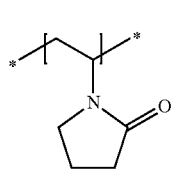

wherein

R¹ and R⁴ are, independently of one another, a hydrogen atom or a methyl group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_8$ to $C_{30}$) alkyl group, and (c) at least one non-ionic film-forming and/or non-ionic setting polymer having structural units according to Formula (I), structural units according to Formula (VII), and structural units according to Formula (VIII)

(I)

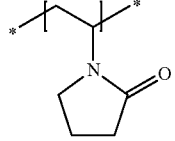

(VII)

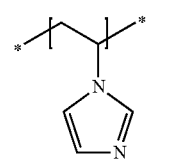

(VIII)

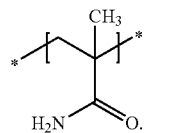

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV), (I)

-continued

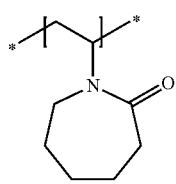
(II)

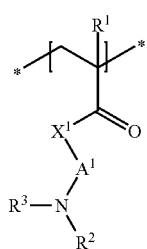
(III)

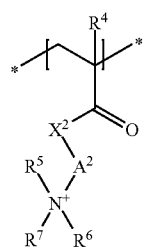
(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one additional cationic film-forming and/or cationic setting polymer having at least one structural unit of Formula (I), at least one structural unit of Formula (VI), and optionally at least one structural unit of Formula (V)

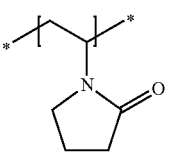
(I)

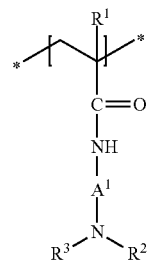
(V)

-continued

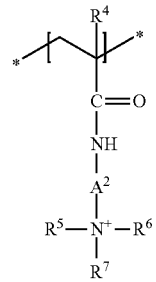
(VI)

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (c) at least one non-ionic film-forming and/or non-ionic setting polymer having at least one structural unit of Formula (I) and at least one structural unit of Formula (III)

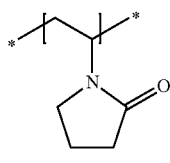
(I)

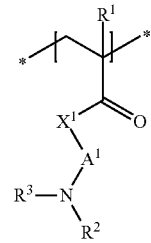
(III)

wherein $R^1$ is a hydrogen atom or a methyl group, $X^1$ is an oxygen atom or an NH group, $A^1$ is an ethane-1,2-diyl, propane-1,3-diyl or butane-1,4-diyl group, $R^2$ and $R^3$ are, independently of one another, a ($C_1$ to $C_4$) alkyl group.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

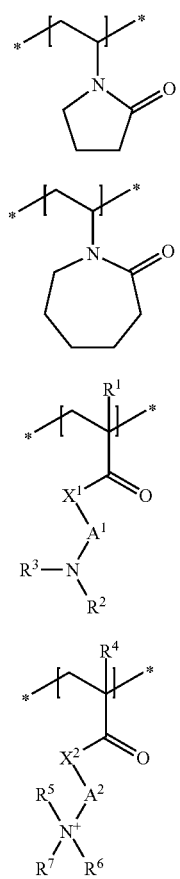

(I)

(II)

(III)

(IV)

wherein

R¹ and R⁴ are, independently of one another, a hydrogen atom or a methyl group,

X¹ and X² are, independently of one another, an oxygen atom or an NH group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_8$ to $C_{30}$) alkyl group, and (b) at least one cationic film-forming and/or cationic setting polymer having at least one structural element of Formula (M1)

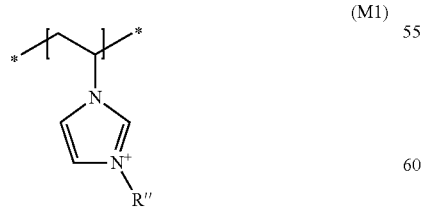

(M1)

wherein R″ is a ($C_1$ to $C_4$) alkyl group, especially a methyl group, and additionally possesses at least one other cationic and/or non-ionic structural element, and (c) polyvinyl pyrrolidone.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

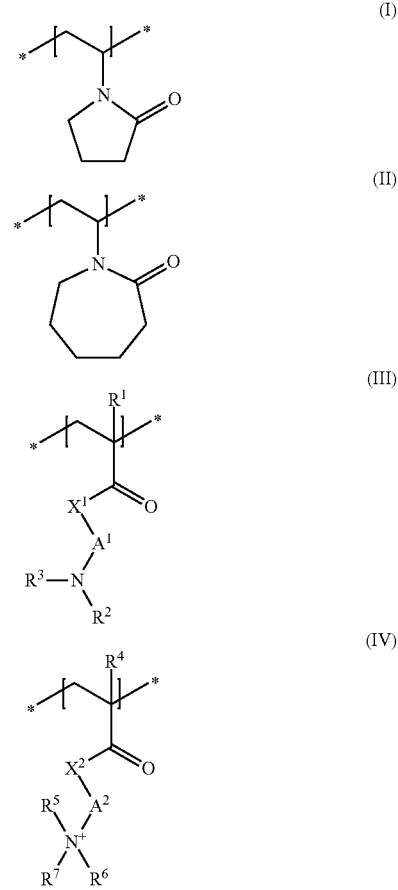

wherein

R¹ and R⁴ are, independently of one another, a hydrogen atom or a methyl group,

X¹ and X² are, independently of one another, an oxygen atom or an NH group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_8$ to $C_{30}$) alkyl group, and (b) at least one cationic film-forming and/or cationic setting polymer having at least one structural element of Formula (M1)

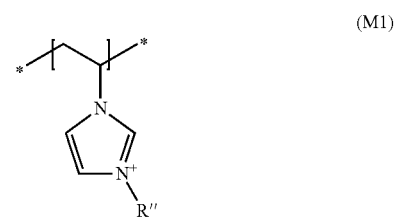

(M1)

wherein R" is a ($C_1$ to $C_4$) alkyl group, particularly methyl, and additionally having at least one further cationic and/or non-ionic structural element; and (c) a copolymer manufactured from monomers N-vinyl pyrrolidone and vinyl acetate, particularly from no additional monomers.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

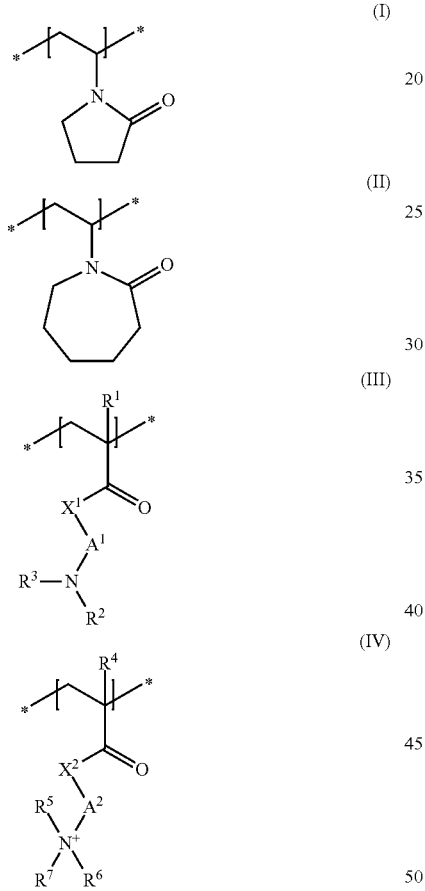

wherein
- $R^1$ and $R^4$ are, independently of one another, a hydrogen atom or a methyl group,
- $X^1$ and $X^2$ are, independently of one another, an oxygen atom or an NH group,
- $A^1$ and $A^2$ are, independently of one another, an ethane-1,2-diyl, propane-1,3-diyl or butane-1,4-diyl group,
- $R^2$, $R^3$, $R^5$ and $R^6$ are, independently of one another, a ($C_1$ to $C_4$) alkyl group,
- $R^7$ is a ($C_3$ to $C_{30}$) alkyl group, and (b) at least one cationic film-forming and/or cationic setting polymer having at least one structural element of Formula (M1)

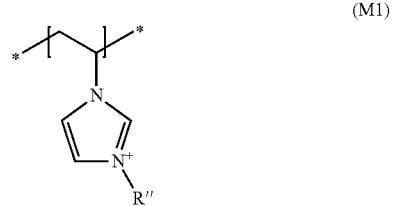

wherein R" is a ($C_1$ to $C_4$) alkyl group, particularly methyl, and additionally having at least one further cationic and/or non-ionic structural element; and (c) at least one non-ionic film-forming and/or non-ionic setting polymer having structural units according to Formula (I), structural units according to Formula (VII), and structural units according to Formula (VIII)

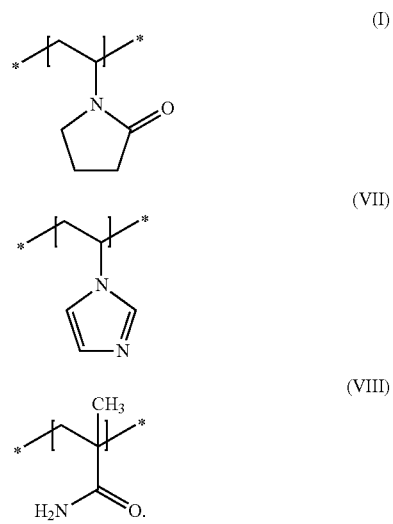

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

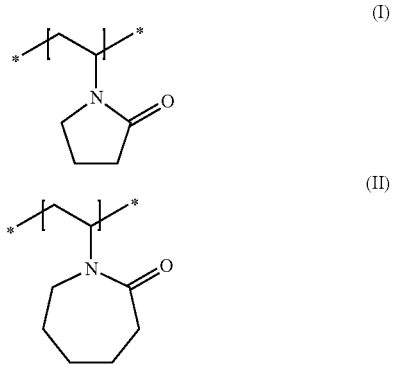

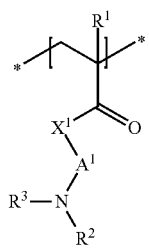
(III)

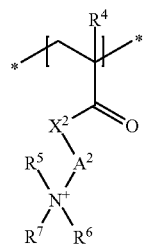
(IV)

wherein

R¹ and R⁴ are, independently of one another, a hydrogen atom or a methyl group,

X¹ and X² are, independently of one another, an oxygen atom or an NH group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_8$ to $C_{30}$) alkyl group, and (b) at least one cationic film-forming and/or cationic setting polymer having at least one structural element of Formula (M1)

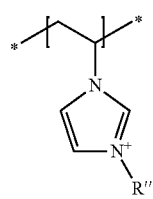
(M1)

wherein R" is a ($C_1$ to $C_4$) alkyl group, particularly methyl, and additionally having at least one further cationic and/or non-ionic structural element; and (c) at least one non-ionic film-forming and/or non-ionic setting polymer having at least one structural unit of Formula (I) and at least one structural unit of Formula (III)

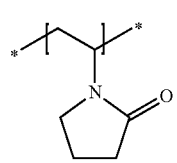
(I)

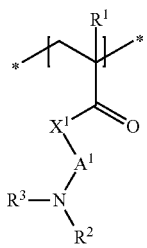
(III)

wherein

R¹ is a hydrogen atom or a methyl group,

X¹ is an oxygen atom or an NH group,

A¹ is an ethane-1,2-diyl, propane-1,3-diyl or butane-1,4-diyl group,

R² and R³ are, independently of one another, a ($C_1$ to $C_4$) alkyl group.

Those agents are particularly preferred that have, in a cosmetically acceptable carrier, (a) at least one amphiphilic, cationic polymer having at least one structural unit of Formula (I), at least one structural unit of Formula (II), at least one structural unit of Formula (III), and at least one structural unit of Formula (IV),

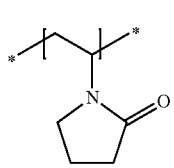
(I)

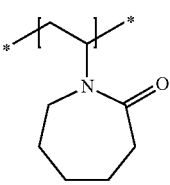
(II)

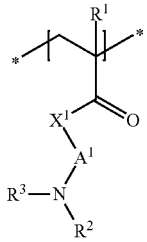
(III)

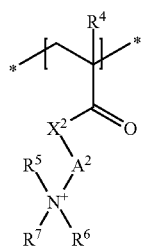
(IV)

wherein

R¹ and R⁴ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one cationic film-forming and/or cationic setting polymer having at least one structural element of Formula (M1) and at least one structural element of Formula (I)

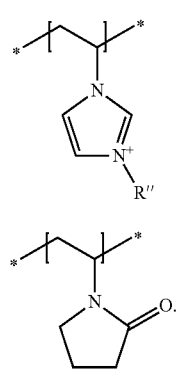

(M1)

(I)

wherein R" is a ($C_1$ to $C_4$) alkyl group, particularly methyl, and additionally having at least one further cationic and/or non-ionic structural element; and (c) polyvinyl pyrrolidone.

Those agents are quite particularly preferred that have in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV),

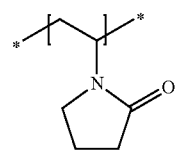

(I)

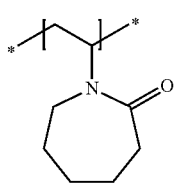

(II)

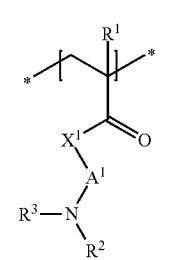

(III)

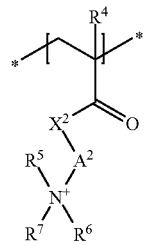

(IV)

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and (b) at least one cationic film-forming and/or cationic setting polymer having at least one structural element of Formula (M1) and at least one structural element of Formula (I)

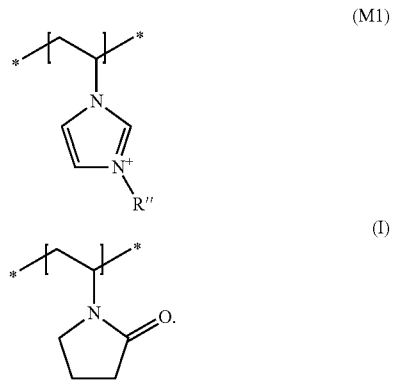

(M1)

(I)

wherein R" is a ($C_1$ to $C_4$) alkyl group, particularly methyl; and (c) a copolymer manufactured from monomers N-vinyl pyrrolidone and vinyl acetate—particularly from no additional monomers.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV),

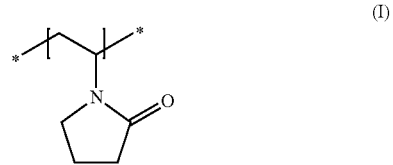

(I)

-continued

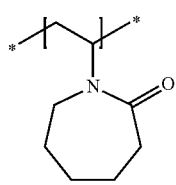 (II)

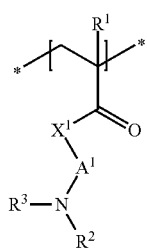 (III)

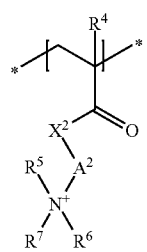 (IV)

wherein
$R^1$ and $R^4$ are, independently of one another, a hydrogen atom or a methyl group,
$X^1$ and $X^2$ are, independently of one another, an oxygen atom or an NH group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group,
$R^7$ is a ($C_8$ to $C_{30}$) alkyl group, and
(b) at least one cationic film-forming and/or cationic setting polymer having at least one structural element of Formula (M1) and at least one structural element of Formula (I)

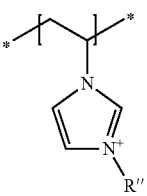 (M1)

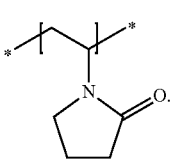 (I)

wherein R" is a ($C_1$ to $C_4$) alkyl group, particularly methyl; and
(c) at least one non-ionic film-forming and/or non-ionic setting polymer having structural units according to Formula (I), structural units according to Formula (VII), and structural units according to Formula (VIII)

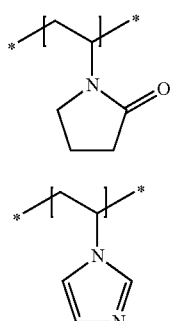 (I)

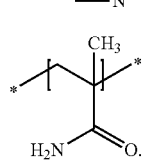 (VII)

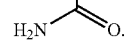 (VIII)

Those agents are particularly preferred that have in a cosmetically acceptable carrier
(a) at least one amphiphilic, cationic polymer having at least one structural unit of Formula (I), at least one structural unit of Formula (II), at least one structural unit of Formula (III), and at least one structural unit of Formula (IV),

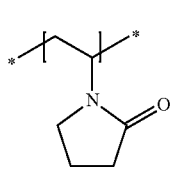 (I)

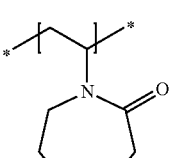 (II)

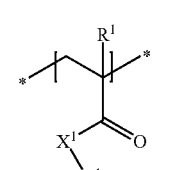 (III)

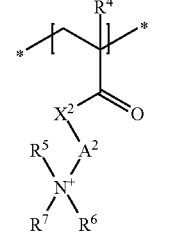 (IV)

wherein

R¹ and R⁴ are, independently of one another, a hydrogen atom or a methyl group,

X¹ and X² are, independently of one another, an oxygen atom or an NH group,

A¹ and A² are, independently of one another, an ethane-1,2-diyl, propane-1,3-diyl or butane-1,4-diyl group, R², R³, R⁵ and R⁶ are, independently of one another, a ($C_1$ to $C_4$) alkyl group, R⁷ is a ($C_3$ to $C_{30}$) alkyl group, and (b) at least one cationic film-forming and/or cationic setting polymer having at least one structural element of Formula (M1) and at least one structural element of Formula (I)

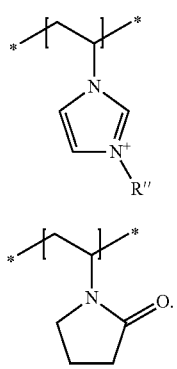

(M1)

(I)

wherein R″ is a ($C_1$ to $C_4$) alkyl group, particularly methyl; and (c) at least one non-ionic film-forming and/or non-ionic setting polymer having at least one structural unit of Formula (I) and at least one structural unit of Formula (III)

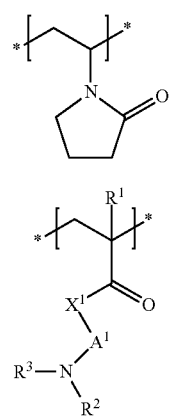

(I)

(III)

wherein

R¹ is a hydrogen atom or a methyl group,

X¹ is an oxygen atom or an NH group,

A¹ is an ethane-1,2-diyl, propane-1,3-diyl or butane-1,4-diyl group,

R² and R³ are, independently of one another, a ($C_1$ to $C_4$) alkyl group.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

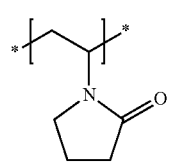

(I)

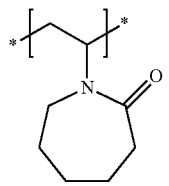

(II)

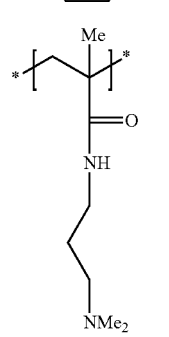

(III-8)

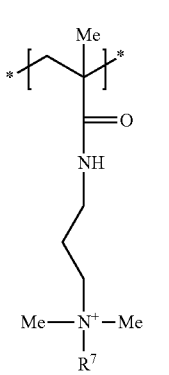

(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives, and (c) polyvinyl pyrrolidone.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

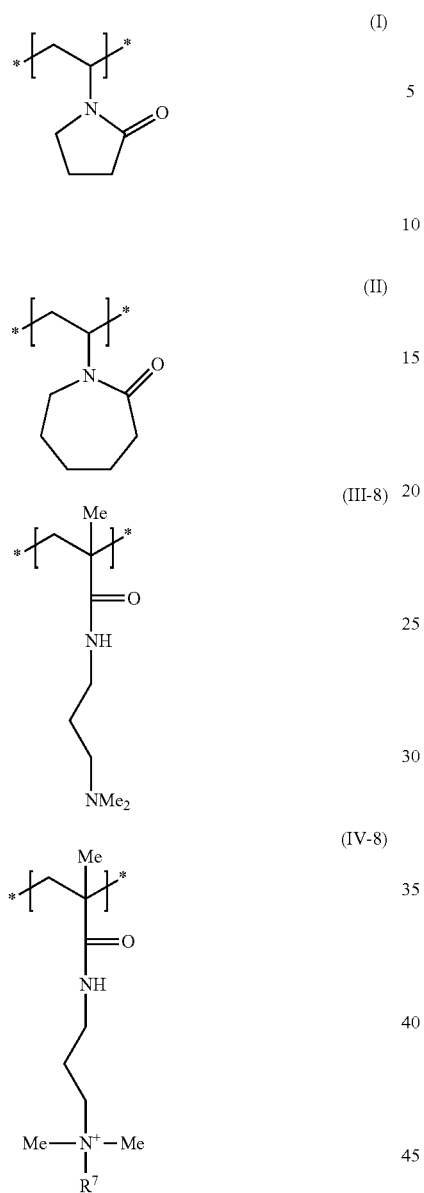

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives, and (c) a copolymer manufactured from monomers N-vinyl pyrrolidone and vinyl acetate—particularly from no additional monomers.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8)

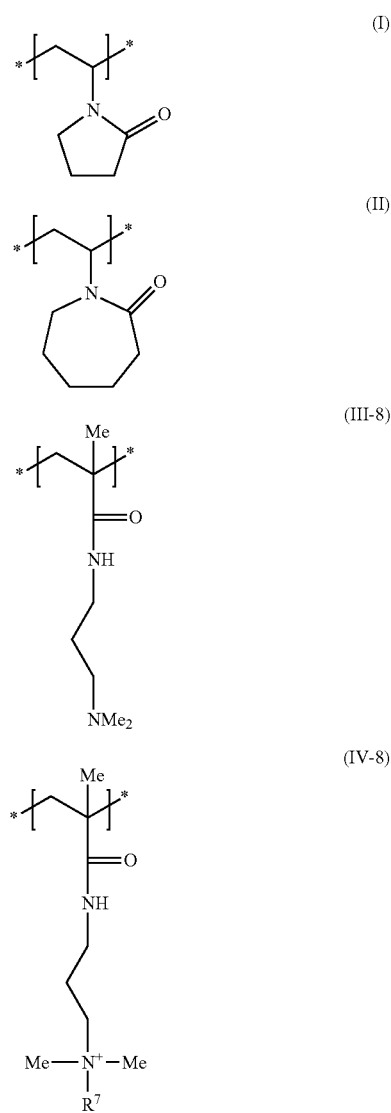

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives, and (c) at least one non-ionic film-forming and/or non-ionic setting polymer having structural units according to Formula (I), structural units according to Formula (VII), and structural units according to Formula (VIII)

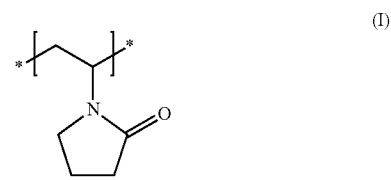

-continued

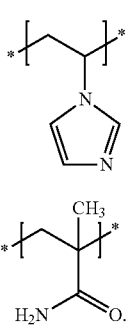
(VII)

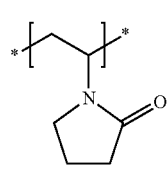
(VIII)

Those agents are particularly preferred that have in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8),

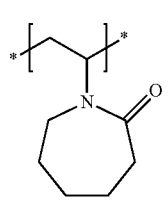
(I)

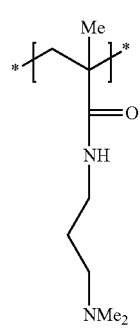
(II)

(III-8)

(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional film-forming cationic and/or setting cationic polymer chosen from cationic, quaternized cellulose derivatives, and (c) at least one non-ionic film-forming and/or non-ionic setting polymer having at least one structural unit of Formula (I) and at least one structural unit of Formula (III)

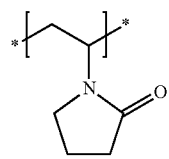
(I)

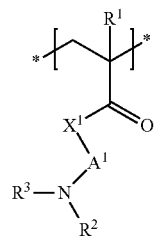
(III)

wherein $R^1$ is a hydrogen atom or a methyl group, $X^1$ is an oxygen atom or an NH group, $A^1$ is an ethane-1,2-diyl, propane-1,3-diyl or butane-1,4-diyl group, $R^2$ and $R^3$ are, independently of one another, a ($C_1$ to $C_4$) alkyl group.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

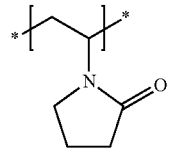
(I)

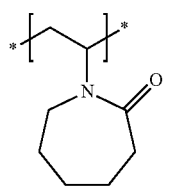
(II)

(III-8)

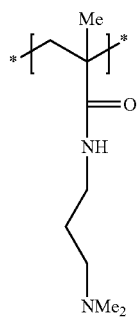

(IV-8)

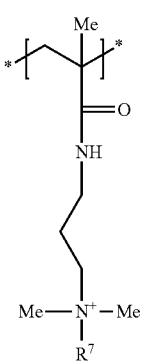

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional cationic film-forming and/or cationic setting polymer having at least one structural unit of Formula (I), at least one structural unit of Formula (VI), and optionally at least one structural unit of Formula (V)

(I)

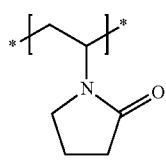

(V)

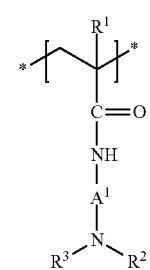

(VI)

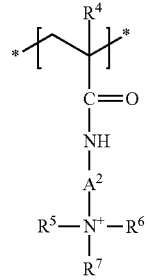

wherein
$R^1$ and $R^4$ are, independently of one another, a hydrogen atom or a methyl group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group,
$R^7$ is a ($C_8$ to $C_{30}$) alkyl group, and (c) polyvinyl pyrrolidone.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8), (I)

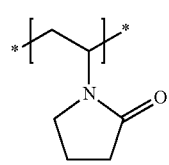

(II)

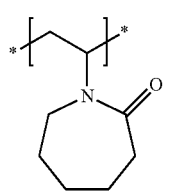

(III-8)

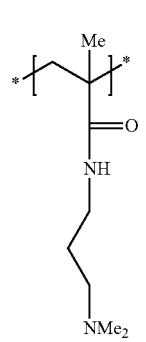

-continued (IV-8)

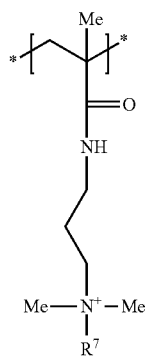

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional cationic film-forming and/or cationic setting polymer having at least one structural unit of Formula (I), at least one structural unit of Formula (VI), and optionally at least one structural unit of Formula (V)

(I)

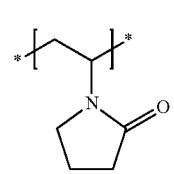

(V)

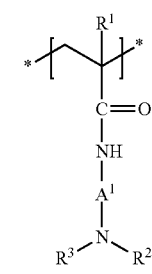

(VI)

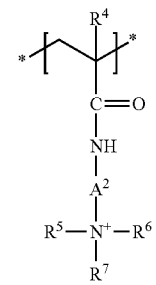

wherein

R¹ and R⁴ are, independently of one another, a hydrogen atom or a methyl group,

A¹ and A² are, independently of one another, an ethane-1,2-diyl, propane-1,3-diyl or butane-1,4-diyl group, R², R³, R⁵ and R⁶ are, independently of one another, a (C₁ to C₄) alkyl group, R⁷ is a (C₈ to C₃₀) alkyl group, and (c) a copolymer manufactured from N-vinyl pyrrolidone and vinyl acetate—particularly from no additional monomers.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8), (I)

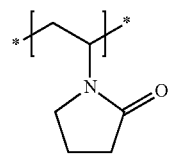

(II)

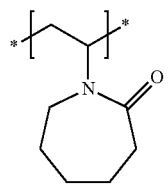

(III-8)

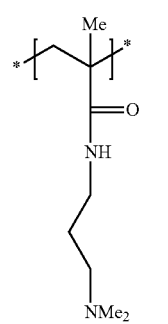

(IV-8)

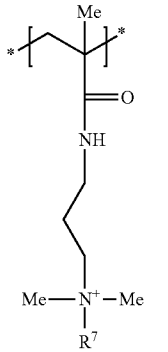

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional cationic film-forming and/or cationic setting polymer having at least one structural unit of Formula (I), at least one structural unit of Formula (VI), and optionally at least one structural unit of Formula (V)

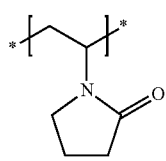
(I)

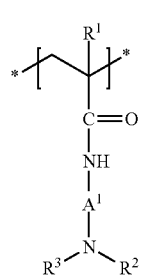
(V)

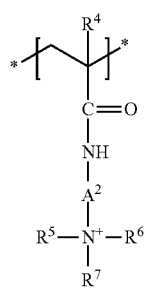
(VI)

wherein
$R^1$ and $R^4$ are, independently of one another, a hydrogen atom or a methyl group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group,
$R^7$ is a ($C_8$ to $C_{30}$) alkyl group, and
(c) at least one non-ionic film-forming and/or non-ionic setting polymer having structural units according to Formula (I), structural units according to Formula (VII) and structural units according to Formula (VIII)

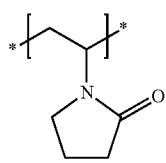
(I)

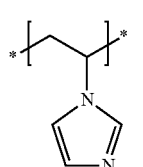
(VII)

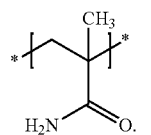
(VIII)

Those agents are particularly preferred that have in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8),

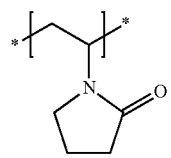
(I)

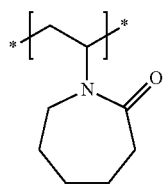
(II)

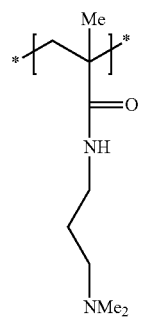
(III-8)

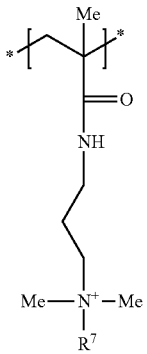
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and
(b) at least one additional cationic film-forming and/or cationic setting polymer having at least one structural unit of Formula (I), at least one structural unit of Formula (VI), and optionally at least one structural unit of Formula (V)

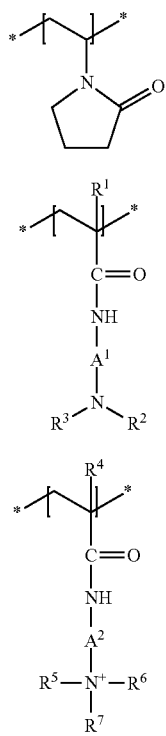 (I)

(V)

(VI)

wherein
$R^1$ and $R^4$ are, independently of one another, a hydrogen atom or a methyl group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group,
$R^7$ is a ($C_8$ to $C_{30}$) alkyl group, and (c) at least one non-ionic film-forming and/or non-ionic setting polymer having at least one structural unit of the Formula (I) and at least one structural unit of the Formula (III)

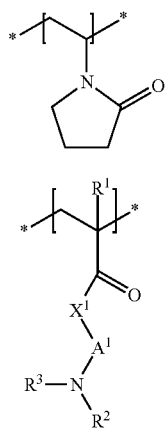

(I)

(III)

wherein
$R^1$ is a hydrogen atom or a methyl group,
$X^1$ is an oxygen atom or an NH group, $A^1$ is an ethane-1,2-diyl, propane-1,3-diyl or butane-1,4-diyl group,
$R^2$ and $R^3$ are, independently of one another, a ($C_1$ to $C_4$) alkyl group.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

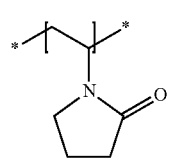 (I)

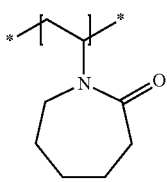 (II)

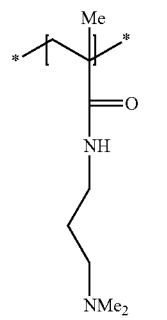 (III-8)

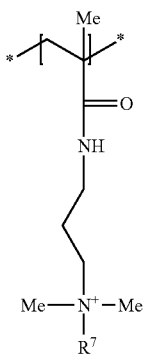 (IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one additional cationic film-forming and/or cationic setting polymer having at least one structural unit of Formula (I), at least one structural unit of Formula (VI-8), and optionally at least one structural unit of Formula (III-8)

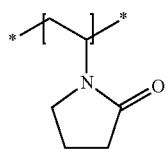
(I)

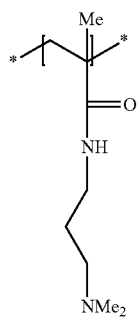
(III-8)

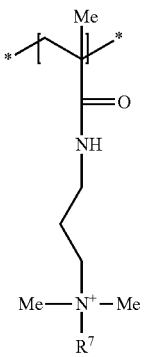
(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (c) at least one non-ionic film-forming and/or non-ionic setting polymer having at least one structural unit of Formula (I) and at least one structural unit of Formula (III-8)

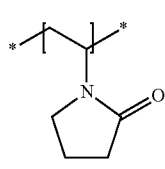
(I)

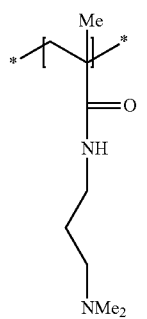
(III-8)

wherein
R¹ is a hydrogen atom or a methyl group,
X¹ is an oxygen atom or an NH group,
A¹ is an ethane-1,2-diyl, propane-1,3-diyl or butane-1,4-diyl group,
R² and R³ are, independently of one another, a ($C_1$ to $C_4$) alkyl group.

The following polymer combinations are quite particularly preferred:
(a) copolymer of N-vinyl pyrrolidone/N-vinyl caprolactam/N-(3-dimethylaminopropyl)methacrylamide and 3-(methacryloylamino)propyl-lauryl-dimethylammonium chloride,
(b) copolymer of N-vinyl pyrrolidone, N,N-dimethylaminopropylmethacrylamide and N,N-dimethyl-N-dodecylammoniopropylmethacrylamide chloride, and
(c) copolymer of N-vinyl pyrrolidone and N,N-dimethylaminopropylmethacrylamide,
(a) copolymer of N-vinyl pyrrolidone/N-vinyl caprolactam/N-(3-dimethylaminopropyl)methacrylamide and 3-(methacryloylamino)propyl-lauryl-dimethylammonium chloride,
(b) dimethylaminoethyl methacrylate-vinyl pyrrolidone copolymer, quaternized with diethyl sulfate, and
(c) copolymer of N-vinyl pyrrolidone and N,N-dimethylaminopropylmethacrylamide.

The above polymer combinations have the INCI names:
(a) Polyquaternium-69 (b) Polyquaternium-55 (c) VP/DMAPA Acrylates Copolymer, and
(a) Polyquaternium-69 (b) Polyquaternium-11 (c) VP/DMAPA Acrylates Copolymer.

Those agents are particularly preferred that have in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8)

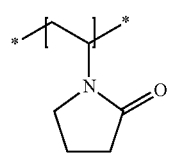
(I)

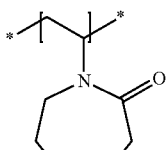
(II)

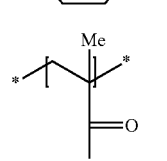
(III-8)

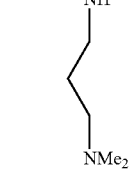

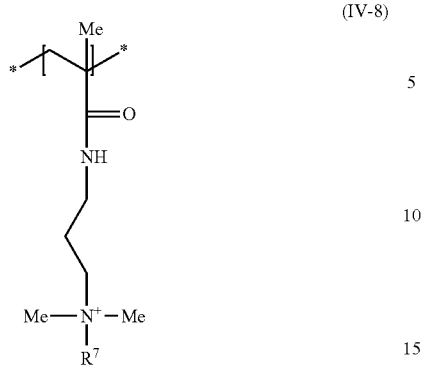

(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1)

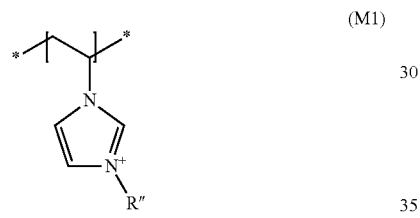

(M1)

wherein R" is a ($C_1$ to $C_4$) alkyl group, particularly methyl, and additionally having another cationic and/or non-ionic structural element, and (c) polyvinyl pyrrolidone.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

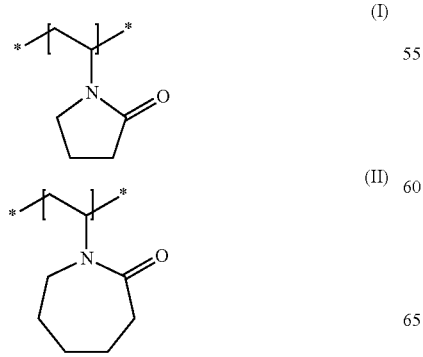

(I)

(II)

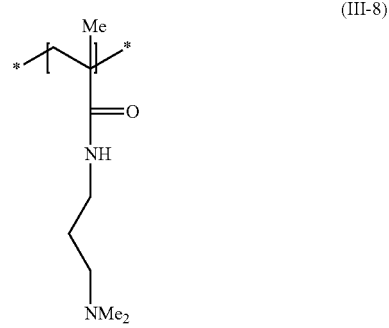

(III-8)

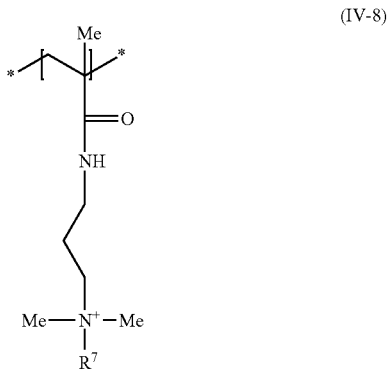

(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1)

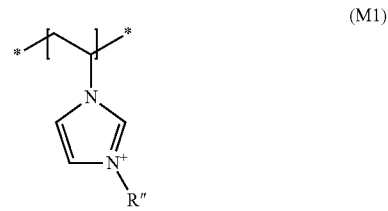

(M1)

wherein R" is a ($C_1$ to $C_4$) alkyl group, particularly methyl, and additionally possessing at least one further cationic and/or non-ionic structural element, and (c) a copolymer manufactured from N-vinyl pyrrolidone and vinyl acetate—particularly from no additional monomers.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

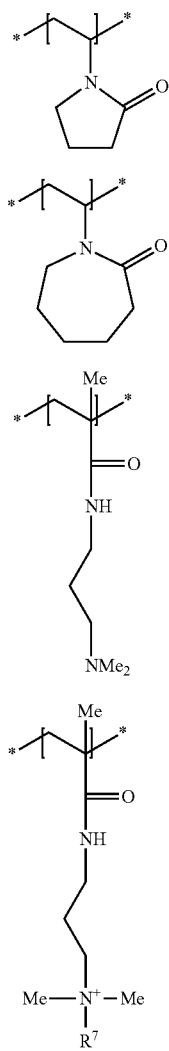

(I)

(II)

(III-8)

(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and
(b) at least one cationic film-forming and/or cationic setting polymer having at least one structural element of Formula (M1)

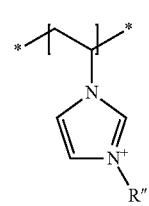

(M1)

wherein R″ is a ($C_1$ to $C_4$) alkyl group, particularly methyl, and
additionally having at least one further cationic and/or non-ionic structural element, and
(c) at least one non-ionic film-forming and/or non-ionic setting polymer having structural units according to Formula (I), structural units according to Formula (VII), and structural units according to Formula (VIII)

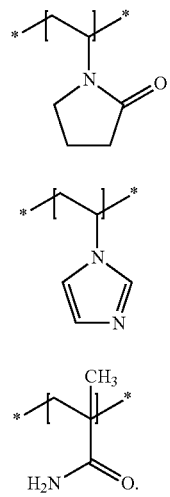

(I)

(VII)

(VIII)

Those agents are particularly preferred that have in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8),

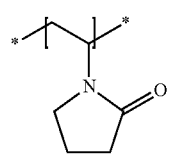

(I)

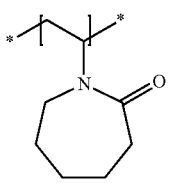

(II)

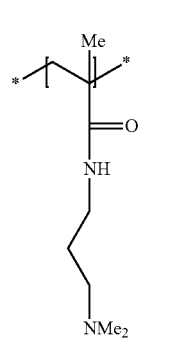

(III-8)

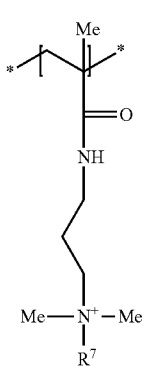

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and
(b) at least one cationic film-forming and/or cationic setting polymer having at least one structural element of Formula (M1)

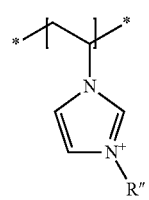

wherein R" is a ($C_1$ to $C_4$) alkyl group, particularly methyl, and
additionally having at least one further cationic and/or non-ionic structural element, and
(c) at least one non-ionic film-forming and/or non-ionic setting polymer having at least one structural unit of Formula (I) and at least one structural unit of Formula (III)

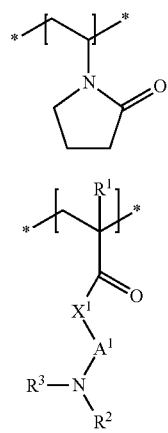

wherein
$R^1$ is a hydrogen atom or a methyl group,
$X^1$ is an oxygen atom or an NH group,
$A^1$ is an ethane-1,2-diyl, propane-1,3-diyl or butane-1, 4-diyl group, and $R^2$ and $R^3$ are, independently of one another, a ($C_1$ to $C_4$) alkyl group.

Those agents are particularly preferred that have in a cosmetically acceptable carrier
(a) at least one amphiphilic, cationic polymer having at least one structural unit of Formula (I), at least one structural unit of Formula (II), at least one structural unit of Formula (III-8), and at least one structural unit of Formula (IV-8),

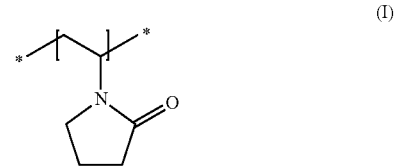

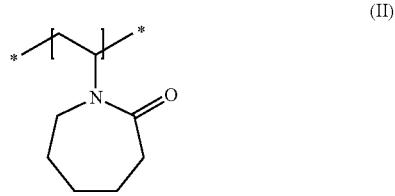

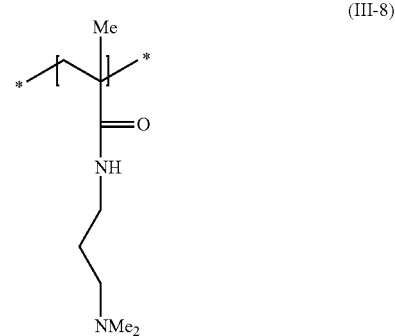

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and
(b) at least one cationic film-forming and/or cationic setting polymer having at least one structural element of Formula (M1) and at least one structural element of Formula (I)

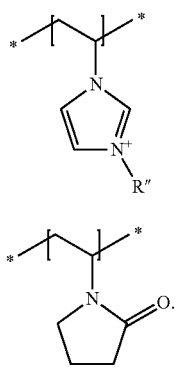 (M1)

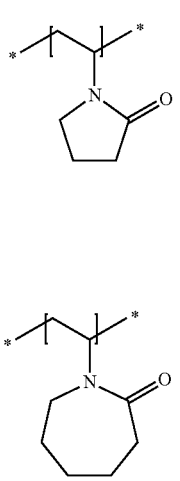 (I)

wherein R" is a ($C_1$ to $C_4$) alkyl group, particularly methyl, and (c) polyvinyl pyrrolidone.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

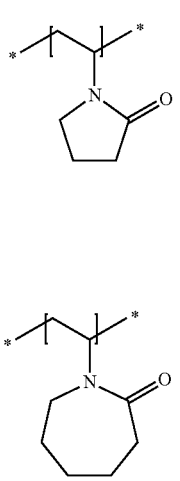 (I)

(II)

(III-8)

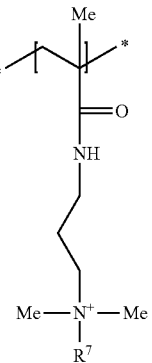 (IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1) and at least one structural element of Formula (I)

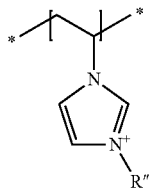 (M1)

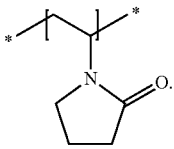 (I)

wherein R" is a ($C_1$ to $C_4$) alkyl group, particularly methyl, and (c) a copolymer manufactured from N-vinyl pyrrolidone and vinyl acetate—particularly from no additional monomers.

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

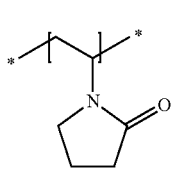 (I)

-continued

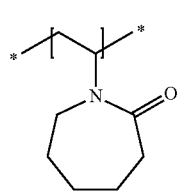
(II)

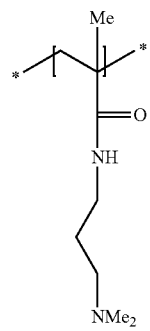
(III-8)

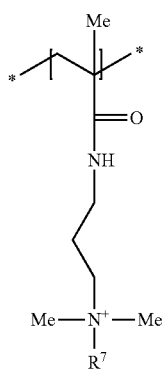
(IV-8)

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1) and at least one structural element of Formula (I)

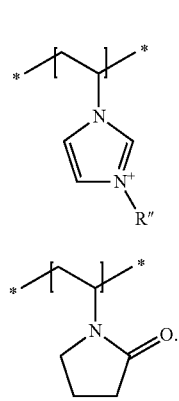
(M1)

(I)

wherein R″ is a ($C_1$ to $C_4$) alkyl group, particularly methyl, and (c) at least one non-ionic film-forming and/or non-ionic setting polymer having structural units according to Formula (I), structural units according to Formula (VII), and structural units according to Formula (VIII)

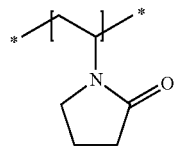
(I)

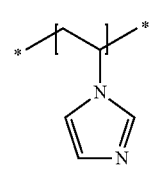
(VII)

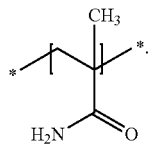
(VIII)

Those agents are particularly preferred that have in a cosmetically acceptable carrier (a) at least one amphiphilic, cationic polymer having at least one structural unit of Formula (I), at least one structural unit of Formula (II), at least one structural unit of Formula (III-8), and at least one structural unit of Formula (IV-8),

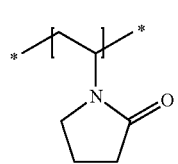
(I)

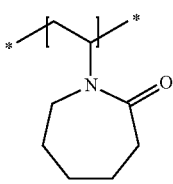
(II)

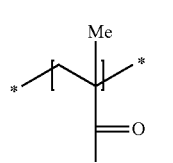
(III-8)

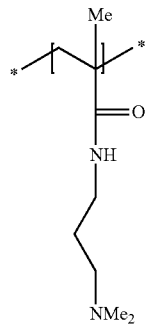

(IV-8)

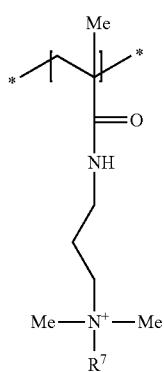

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one cationic film-forming and/or cationic setting polymer having at least one structural element of Formula (M1) and at least one structural element of Formula (I)

(M1)

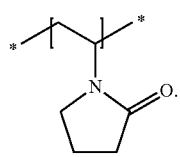

wherein R″ is a ($C_1$ to $C_4$) alkyl group, particularly methyl, and (c) at least one non-ionic film-forming and/or non-ionic setting polymer having at least one structural unit of Formula (I) and at least one structural unit of Formula (III)

(I)

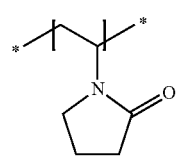

(III)

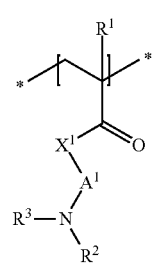

wherein
$R^1$ is a hydrogen atom or a methyl group,
$X^1$ is an oxygen atom or an NH group,
$A^1$ is an ethane-1,2-diyl, propane-1,3-diyl or butane-1,4-diyl group,
$R^2$ and $R^3$ are, independently of one another, a ($C_1$ to $C_4$) alkyl group.

The following polymer combinations are quite particularly preferred:
(a) copolymer of N-vinyl pyrrolidone/N-vinyl caprolactam/N-(3-dimethylaminopropyl)methacrylamide and 3-(methacryloylamino)propyl-lauryl-dimethylammonium chloride,
(b) 3-methyl-1-vinylimidazolium chloride-vinyl pyrrolidone copolymer, and
(c) copolymer of N-vinyl pyrrolidone and N,N-dimethylaminopropylmethacrylamide.
(a) copolymer of N-vinyl pyrrolidone/N-vinyl caprolactam/N-(3-dimethylaminopropyl)methacrylamide and 3-(methacryloylamino)propyl-lauryl-dimethylammonium chloride,
(b) vinyl pyrrolidone-methacrylamide-vinyl imidazol-vinylimidazolium methosulfate copolymer, and
(c) copolymer of N-vinyl pyrrolidone and N,N-dimethylaminopropylmethacrylamide.

The abovementioned polymer combinations have the INCI names:
(a) Polyquaternium-69 (b) Polyquaternium-16 (c) VP/DMAPA Acrylates Copolymer; and
(a) Polyquaternium-69 (b) Polyquaternium-68 (c) VP/DMAPA Acrylates Copolymer.

In the context of all these embodiments, the previously cited preferred embodiments of amphiphilic, cationic polymer (a) are preferred (see above). Similarly, all previously mentioned quantitative data regarding polymer components (a), (b) and (c) of the agent are also preferred mutatis mutandis for these embodiments.

In order to intensify the effect, the agents preferably additionally comprise at least one surfactant, wherein, in principal, non-ionic, anionic, cationic, ampholytic surfactants are suitable. Ampholytic or amphoteric surfactants include zwitterionic surfactants and ampholytes. According to the invention, the surfactants can already have an emulsifying action.

The agent preferably contains surfactants in an amount of 0.01 wt. % to 5 wt. %, particularly preferably 0.05 wt. % to 0.5 wt. %, based on total weight of the agent.

It has proved particularly preferable when the agents have at least one non-ionic surfactant.

Non-ionic surfactants can include a polyol group, a polyalkylene glycol ether group, or a combination of polyol ether groups and polyglycol ether groups as the hydrophilic group.

Exemplary compounds of this type are—
addition products of 2 to 100 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group, methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as the commercially available products Dehydrol® LS, Dehydrol® LT (Cognis), $C_{12}$-$C_{30}$ fatty acid mono- and diesters of addition products of 1 to 30 moles ethylene oxide to glycerin, addition products of 5 to 60 moles ethylene oxide on castor oil and hydrogenated castor oil, polyol esters of fatty acids, such as the commercial product Hydagen® HSP (Cognis) or Sovermol types (Cognis), alkoxylated triglycerides, alkoxylated alkyl esters of fatty acids of Formula (E4-I), $$R^1CO\text{—}(OCH_2CHR_2)_wOR^3 \quad (E4\text{-}I)$$

wherein $R^1CO$ is a linear or branched, saturated and/or unsaturated acyl group with 6 to 22 carbon atoms, $R^2$ is hydrogen or methyl, $R^3$ is linear or branched alkyl groups with 1 to 4 carbon atoms and w is a number from 1 to 20, amine oxides, mixed hydroxy ethers, such as are described in DE-OS 1 973 8866, sorbitol esters of fatty acids and addition products of ethylene oxide to sorbitol esters of fatty acids such as polysorbates, sugar esters of fatty acids and addition products of ethylene oxide to sugar esters of fatty acids, addition products of ethylene oxide to fatty acid alkanolamides and fatty amines, sugar surfactants of the type alkyl and alkenyl oligoglycosides according to Formula (E4-II), $$R^4O\text{—}[G]_p \quad (E4\text{-}II)$$

wherein $R^4$ is an alkyl or alkenyl group containing 4 to 22 carbon atoms, G is a sugar group containing 5 or 6 carbon atoms, and p is a number from 1 to 10.

Alkylene oxide addition products to saturated, linear fatty alcohols and fatty acids, each with 2 to 100 moles ethylene oxide per mole fatty alcohol or fatty acid, have proved to be quite particularly preferred non-ionic surfactants. Similarly, preparations with excellent properties are obtained when they comprise $C_{12}$-$C_{30}$ fatty acid mono- and diesters of addition products of 1 to 30 moles ethylene oxide to glycerin and/or addition products of 5 to 60 moles ethylene oxide to castor oil and hydrogenated castor oil as the non-ionic surfactants.

Suitable anionic surfactants include all anionic surface-active materials suitable for use on the human body. They have a water solubilizing anionic group, such as a carboxylate, sulfate, sulfonate or phosphate group, and a lipophilic alkyl group containing about 8 to 30 carbon atoms. In addition, the molecule may comprise glycol or polyglycol ether groups, ester, ether and amide groups as well as hydroxyl groups. Exemplary suitable anionic surfactants are, each in the form of the sodium, potassium and ammonium as well as the mono, di and trialkanolammonium salts containing 2 to 4 carbon atoms in the alkanol group, linear and branched fatty acids with 8 to 30 carbon atoms (soaps), ether carboxylic acids of the formula R—O—($CH_2$—$CH_2O)_x$—$CH_2$—COOH, wherein R is a linear alkyl group with 8 to 30 carbon atoms and x=0 or 1 to 16, acyl sarcosides with 8 to 24 carbon atoms in the acyl group, acyl taurides with 8 to 24 carbon atoms in the acyl group, acyl isethionates with 8 to 24 carbon atoms in the acyl group, mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups, linear alkane sulfonates containing 8 to 24 carbon atoms, linear alpha-olefin sulfonates containing 8 to 24 carbon atoms, alpha-sulfo fatty acid methyl esters of fatty acids containing 8 to 30 carbon atoms, alkyl sulfates and alkyl polyglycol ether sulfates of the Formula R—O($CH_2$—$CH_2O)_x$—$OSO_3H$, wherein R preferably is a linear alkyl group containing 8 to 30 carbon atoms and x=0 or 1 to 12, mixtures of surface active hydroxyl sulfonates, sulfated hydroxyalkyl polyethylene glycol ethers and/or hydroxyalkylene propylene glycol ethers, sulfonates of unsaturated fatty acids with 8 to 24 carbon atoms and 1 to 6 double bonds, esters of tartaric acid and citric acid with alcohols, which represent the addition products of about 2-15 molecules of ethylene oxide and/or propylene oxide on fatty alcohols containing 8 to 22 carbon atoms, sulfated fatty acid alkylene glycol esters of Formula (E1-II)

$$R^7CO(AlkO)_nSO_3M \quad (E1\text{-}II)$$

wherein $R^7CO$— is a linear or branched, aliphatic, saturated and/or unsaturated acyl group containing 6 to 22 carbon atoms, Alk is $CH_2CH_2$, $CHCH_3CH_2$ and/or $CH_2CHCH_3$, n is a number from 0.5 to 5, and M is a cation, as described in DE-OS 197 36 906, amide ether carboxylic acids, and condensation products of $C_8$-$C_{30}$ fatty alcohols with protein hydrolyzates and/or amino acids and their derivatives, known to one skilled in the art as albumin fatty acid condensates, such as the Lamepon® types, Gluadin® types, Hostapon® KCG or Amisoft® types.

Preferred anionic surfactants are alkyl sulfates and ether carboxylic acids having 10 to 18 carbon atoms in the alkyl group and up to 12 glycol ether groups in the molecule, sulfosuccinic acid mono and dialkyl esters having 8 to 18 C atoms in the alkyl group and sulfosuccinic acid mono-alkyl polyoxyethyl esters having 8 to 18 C atoms in the alkyl group and 1 to 6 oxyethylene groups, monoglycerin disulfates, alkyl- and alkenyl ether phosphates, as well as albumin fatty acid condensates.

Zwitterionic surfactants refer to those surface-active compounds having at least one quaternary ammonium group and at least one —$COOS^{(-)}$ or —$SO_3^{(-)}$ group in the molecule. Particularly suitable zwitterionic surfactants are betaines such as N-alkyl-N,N-dimethylammonium glycinates, for example, cocoalkyl-dimethylammonium glycinate, N-acyl-aminopropyl-N,N-dimethylammonium glycinate, for example, coco-acylaminopropyl-dimethylammonium glycinate, and 2-alkyl-3-carboxymethyl-3-hydroxyethyl-imidazolines, each having 8 to 18 carbon atoms in the alkyl or acyl group, as well as cocoacyl-aminoethylhydroxyethylcarboxymethyl glycinate. A preferred zwitterionic surfactant is the fatty acid amide derivative known under the INCI name Cocamidopropyl Betaine.

Ampholytes include such surface-active compounds that, apart from a $C_{8-24}$ alkyl or acyl group, have at least one free amino group and at least one —COOH or —$SO_3H$ group in the molecule, and are able to form internal salts. Examples of suitable ampholytes are N-alkylglycines, N-alkyl propionic acids, N-alkylamino butyric acids, N-alkylimino dipropionic acids, N-hydroxyethyl-N- alkylamidopropylglycines, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and $C_{12-18}$ acyl sarcosine.

Agents according to the invention contain ingredients or active substances in a cosmetically acceptable carrier. Preferred cosmetically acceptable carriers are aqueous, alcoholic or aqueous alcoholic media containing preferably at least 10 wt. % water, based on total composition. In particular, lower alcohols having 1 to 4 carbon atoms such as ethanol and isopropanol, typically used for cosmetic purposes, can be used as alcohols.

Organic solvents or mixture of solvents with a boiling point of less than 400° C. can be used as additional co-solvents in an amount of 0.1 to 15 weight percent, preferably 1 to 10 weight percent, based on total weight of the agent. Particularly suitable additional co-solvents are unbranched or branched hydrocarbons such as pentane, hexane, isopentane and cyclic hydrocarbons such as cyclopentane and cyclohexane. Additional, particularly preferred water-soluble solvents are glycerin, ethylene glycol and propylene glycol in an amount of up to 30 weight percent based on total weight of the agent.

In particular, the addition of glycerin and/or propylene glycol and/or polyethylene glycol and/or polypropylene glycol increases the flexibility of the polymer film formed when an agent according to the invention is used. Consequently, if a more flexible hold is desired, then the agents preferably has 0.01 to 30 wt. % glycerin and/or propylene glycol and/or polyethylene glycol and/or polypropylene glycol, based on total weight of the agent.

The agents preferably have a pH of 2 to 11. The pH range is more preferably from 2 to 8. In the context of this publication, pH data refer to pH at 25° C. unless otherwise stated.

The agents can also contain auxiliaries and additives typically incorporated into styling agents. In particular, care products may be mentioned as suitable auxiliaries and additives. According to the invention, at least one silicone oil and/or at least one silicone gum is preferably employed as the care substance.

Suitable silicone oils or silicone gums according to the invention include dialkyl and alkylarylsiloxanes such as dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils afford the most varied effects. Thus, for example, they simultaneously influence dry and wet combability and feel of the dry and wet hair, as well as the gloss. The term, "silicone oils" is understood by one skilled in the art to mean organosilicon compounds with a plurality of structures. In the first instance they include the Dimethiconols.

The following commercial products are given as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzene sulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel S11400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), San-Surf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-SiI CD-1, Taylor TME-4050E (all from Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones form the second group of silicones that can be used according to the invention. They can be linear, branched, cyclic, or cyclic and branched. Dimethicone copolyols form a further group of suitable silicones. Suitable Dimethicone copolyols are commercially available and marketed, for example, by Dow Corning under the trade name Dow Corning® 5330 Fluid.

Naturally, the invention also allows for use of Dimethiconols, Dimethicones and/or Dimethicone copolymers already present as an emulsion. When the Dimethiconols, Dimethicones and/or Dimethicone copolyols are used as an emulsion, then droplet size of the emulsified particles ranges from 0.01 to 10,000 µm, preferably 0.01 to 100 µm, particularly preferably 0.01 to 20 µm, and quite particularly preferably 0.01 to 10 µm. Particle size is determined here according to the light scattering method.

Further suitable silicones are amino-functional silicones, particularly silicones listed under the INCI name Amodimethicone. Consequently, it is inventively preferred when the agents also have at least one amino-functional silicone. These are silicones having at least one, optionally substituted, amino group. These silicones are designated as Amodimethicones according to the INCI nomenclature and are available, for example, in the form of an emulsion as the commercial product Dow Corning® 939 or as the commercial product Dow Corning® 949 in a mixture with a cationic and a non-ionic surfactant.

Preferably, those amino functional silicones are used which have an amine number of 0.25 meq/g or greater, preferably 0.3 meq/g or greater, and particularly preferably 0.4 meq/g or greater. The amine number is the milli-equivalents of amine per gram of the amino functional silicone. It can be measured by titration and can also be reported with the unit mg KOH/g.

The agents preferably contain silicones in amounts of 0.01 wt. % to 15 wt. %, particularly preferably 0.05 to 2 wt. %, based on total weight of the agent.

The composition can optionally include at least one protein hydrolyzate and/or one of its derivatives as a care substance of another compound class. The agents contain protein hydrolyzates, for example, in concentrations of 0.01 wt. % to 20 wt. %, preferably 0.05 wt. % up to 15 wt. %, and quite particularly preferably in amounts of 0.05 wt. % up to 5 wt. %, based on total weight of the end-use preparation.

The agents can further include at least one vitamin, one provitamin, one vitamin precursor and/or one of their derivatives as the care substance.

According to the invention, such vitamins, provitamins and vitamin precursors are preferred which are normally classified in the groups A, B, C, E, F and H. Retinol (vitamin $A_1$) as well as 3,4-didehydroretinol, (vitamin $A_2$) belong in the group of substances designated as vitamin A. The vitamin B group or vitamin B complex include, inter alia, vitamin $B_1$ (thiamine), vitamin $B_2$ (riboflavin), vitamin $B_3$ (nicotinic acid and/or nicotinic acid amide (niacinamide)), vitamin $B_5$ (pantothenic acid, panthenol and pantolactone), vitamin $B_6$ (pyridoxine as well as pyridoxamine and pyridoxal). Other representatives of the abovementioned vitamins are vitamin C (ascorbic acid), vitamin E (tocopherols, especially α-tocopherol), vitamin F (linoleic acid and/or linolenic acid), vitamin H.

Agents according to the invention preferably contain vitamins, provitamins and vitamin precursors from groups A, B, C, E and H. Panthenol, pantolactone, pyridoxine and its derivatives, as well as nicotinamide and biotin are especially preferred. D-panthenol is quite particularly preferably used as a care substance, optionally in combination with at least one of the abovementioned silicone derivatives.

Thus, if a particularly flexible hold is desired, then the agents can include panthenol instead of or in addition to glycerin and/or propylene glycol. In a preferred embodiment, the agents contain panthenol, preferably in a quantity of 0.05 to 10 wt. %, particularly preferably 0.1 to 5 wt. %, based on total weight of the agent.

The agents can further contain at least one plant extract as a care substance. Usually, these extracts are manufactured by extraction of the whole plant. In individual cases, however, it can also be preferred to produce the extracts solely from blossoms and/or leaves of the plant. According to the invention, extracts mainly from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger are preferred.

The agent can further comprise at least one lipid as a care substance. According to the invention, suitable lipids are phospholipids, for example, soy lecithin, egg lecithin and cephalins as well as substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EFA®, Phospholipid PTC® and Phospholipid SV®. The agents according to the invention preferably contain lipids in amounts of 0.01 to 10 wt. %, in particular 0.1 to 5 wt. %, based on total weight of the end-use preparation.

Oil bodies are also suitable as a care substance. Natural and synthetic cosmetic oil bodies include— vegetal oils. Examples of such oils are sunflower oil, olive oil, soya oil, rapeseed oil, almond oil, jojoba oil, orange oil, wheat germ oil, peach stone oil and the liquid parts of coconut oil. Other triglyceride oils such as the liquid fractions of beef tallow as well as synthetic triglyceride oils are also suitable.

liquid paraffin oils, isoparaffin oils and synthetic hydrocarbons as well as di-n-alkyl ethers containing a total of 12 to 36 carbon atoms, particularly 12 to 24 carbon atoms such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-ethyldecyl ether, tert.butyl n-octyl ether, isopentyl n-octyl ether and 2-methylpentyl n-octyl ether. The commercial products of the compounds 1,3-di-(2-ethylhexyl)cyclohexane (Cetiol® S) and di-n-octyl ether (Cetiol® OE) can be preferred.

Ester oils. Ester oils are understood to mean the esters of $C_6$-$C_{30}$ fatty acids with $C_2$-$C_{30}$ fatty alcohols. Monoesters of fatty acids with alcohols having 2 to 24 carbon atoms are preferred. According to the invention, isopropyl myristate (Rilanit® IPM), isononanoic acid $C_{16\text{-}18}$ alkyl ester (Cetiol® SN), 2-ethylhexyl palmitate (Cegesoft® 24), stearic acid 2-ethylhexyl ester (Cetiol® 868), cetyl oleate, glycerin tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

Dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butane diol di-isostearate, neopentyl glycol dicaprylate, symmetrical, unsymmetrical or cyclic esters of carbon dioxide with fatty alcohols, for example, as described in DE-OS 197 56 454, glycerine carbonate or dicaprylyl carbonate (Cetiol® CC), trifatty acid esters of saturated and/or unsaturated linear and/or branched fatty acids with glycerin, fatty acid partial glycerides, under which are understood monoglycerides, diglycerides and their industrial mixtures. When using industrial products, minor amounts of triglycerides may still be contained as a result of the production process. The partial glycerides preferably comply with the Formula (D4-I),

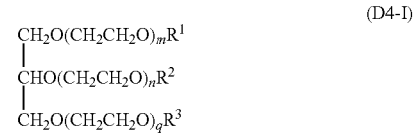
(D4-I)

wherein $R^1$, $R^2$ and $R^3$ are, independently of each other, hydrogen or for a linear or branched, saturated and/or unsaturated acyl group containing 6 to 22 carbon atoms, preferably 12 to 18 carbon atoms, with the proviso that at least one of these groups is an acyl group and at least one of these groups is hydrogen. The sum of (m+n+q) is 0 or a number from 1 to 100, preferably 0 or 5 to 25. Preferably, $R^1$ is an acyl group, $R^2$ and $R^3$ are hydrogen, and the sum of (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The amount of natural and synthetic cosmetic oil bodies added to the agents according to the invention is usually 0.1 to 30 wt. %, based on total weight of the end-use preparation, preferably 0.1 to 20 wt. % and particularly 0.1 to 15 wt. %.

By addition of a UV filter, both the agent as well as the treated fibers can be protected against damage from UV radiation. Consequently, at least one UV filter is preferably added to the agent. Suitable UV filters are not generally limited with respect to their structure and their physical properties. Indeed, all UV filters that can be used in the cosmetic field having an absorption maximum in the UVA (315-400 nm), UVB (280-315 nm) or UVC (<280 nm) regions are suitable. UV filters having an absorption maximum in the UVB region, especially in the range from about 280 to about 300 nm, are particularly preferred. Preferred UV-filters are chosen from substituted benzophenones, p-aminobenzoates, diphenylacrylates, cinnamates, salicylates, benzimidazoles and o-aminobenzoates.

The agent usually contains UV filters in amounts of 0.01 to 5 wt. %, based on total weight of the end-use preparation. Quantities of 0.1 to 2.5 wt. % are preferred.

In a particular embodiment, the agent further includes one or more substantive dyes. Application of the agent then enables the treated keratinic fiber not only to be temporarily styled, but also to be dyed at the same time. This can be particularly desirable when only a temporary dyeing is desired, for example, with flamboyant fashion colors that can be subsequently removed from the keratinic fibers by simply washing them out. Substantive dyes are usually nitrophenylenediamines, nitroamino phenols, azo dyes, anthraquinones, indophenols or cationic substantive dyes are employed. Particularly preferred cationic dyes are

- cationic triphenylmethane dyes, such as Basic Blue 7, Basic Blue 26, Basic Violet 2 and Basic Violet 14,
- aromatic systems which are substituted by a quaternary nitrogen group, such as Basic Yellow 57, Basic Red 76, Basic Blue 99, Basic Brown 16 and Basic Brown 17, and
- substantive dyes having a heterocycle possessing at least one quaternary nitrogen atom. The dyes, also known under the names Basic Yellow 87, Basic Orange 31 and Basic Red 51, are quite particularly preferred cationic substantive dyes here.

Cationic substantive dyes commercialized under the trade name Arianor® are likewise quite particularly preferred cationic substantive dyes according to the invention. In addition, compositions according to the invention can also comprise naturally occurring dyestuffs as are found, for example, in henna red, hernia neutral, henna black, camomile leaves, sandalwood, black tea, alder buckthorn bark, sage, logwood, madder root, cachou, cedar and alkanet root.

Agents according to this embodiment contain substantive dyes preferably in an amount of 0.001 to 20 wt. %, based on total weight of the agent.

It is inventively preferred for the agents to be exempt from oxidation dye precursors. Oxidation dye precursors are divided into developer components and coupler components. Under the influence of oxidizing agents or from atmospheric oxygen, developer components form the actual colorants among each other or by coupling with one or more coupler components.

Formulation of the agents can be in all usual forms for styling agents, for example, as solutions that can be applied as hair water or pump or aerosol spray onto the hair, as creams, emulsions, waxes, gels or surfactant-containing foaming solutions or other preparations are suitable for application on the hair.

Hair creams and hair gels generally include structurants and/or thickening polymers which lend the desired consistency to the products. Structurants and/or thickening polymers are typically added in amounts of 0.1 to 10 wt. %, based on total weight of the product. Quantities of 0.5 to 5 wt. %, particularly 0.5 to 3 wt. %, are preferred.

The agents are preferably in the form of a pump spray, aerosol spray, pump foam or aerosol foam.

For this, agents according to the invention are packaged in a dispensing device, illustrated by either a pressurized gas container additionally containing a propellant ("aerosol container") or by a non-aerosol container.

Pressurized gas containers by which a product is dispersed through a valve by the internal gas pressure in the container are defined as "aerosol containers". The opposite of the aerosol definition, a container under normal pressure, is defined as a "non-aerosol container", from which a product is dispersed by mechanical actuation of a pump system.

Agents according to the invention are preferably packed as an aerosol hair foam or aerosol hair spray. Consequently, the agent additionally has at least one propellant.

Suitable exemplary propellants include $N_2O$, dimethyl ether, $CO_2$, air, alkanes containing 3 to 5 carbon atoms, such as propane, n-butane, iso-butane, n-pentane and iso-pentane, and their mixtures. Dimethyl ether, propane, n-butane, iso-butane and their mixtures are preferred.

According to a preferred embodiment, the alkanes, mixtures of the alkanes or mixtures of the alkanes with dimethyl ether are preferred as the sole propellant. However, the invention also includes joint utilization with propellants of the fluorochlorohydrocarbon type, especially fluorinated hydrocarbons.

With respect to the weight ratio of propellant to the usual ingredients of the preparation, the size of the aerosol droplets or the foam bubbles and the relevant size distribution can be adjusted for a given spray device.

The amount of added propellant varies based on actual composition of the agent, packaging used, and the desired product type, for example, hair spray or hair foam. When a conventional spray device is used, aerosol foam products preferably contain propellant in amounts of 1 to 35 wt. %, based on total weight of the product. Quantities of 2 to 30 wt. %, especially 3 to 15 wt. %, are particularly preferred. Aerosol sprays generally contain greater amounts of propellant. Here, the propellant is preferably added in amounts of 30 to 98 wt. %, based on total weight of the product. Quantities of 40 to 95 wt. %, especially 50 to 95 wt. %, are particularly preferred.

Aerosol products can be manufactured according to conventional techniques. Generally, all ingredients of the agent except the propellant are charged into a suitable pressure-resistant container. This is then sealed with a valve. The desired amount of propellant is then filled using conventional techniques.

Agents in the form of gels are foamed in a two-chamber aerosol container, preferably with isopentane as the propellant, which is incorporated into the agent and packed in the first chamber of the two-chamber aerosol container. At least one additional propellant different from isopentane is packed in the second chamber of the two-chamber aerosol container and generates a higher pressure than the isopentane. The propellants of the second chamber are preferably chosen from $N_2O$, dimethyl ether, $CO_2$, air, alkanes containing 3 or 4 carbon atoms (such as propane, n-butane, iso-butane) as well as mixtures thereof.

Aerosol hair foams or aerosol hair sprays containing the above described agent according to the invention and at least one propellant are a preferred embodiment of the agent.

Preferred agents and propellants of the aerosol hair foam or aerosol hair spray, as well as the relevant amounts of propellant, correspond to those already mentioned above.

A second subject matter of the invention is use of the agent for the temporary shaping of hair and/or for hair care.

The agents and products containing these agents, particularly aerosol hair foams or aerosol hair sprays, lend to the treated hair a very strong, long-lasting hold to the hairstyle, while the hair remains flexible. If the agent is in the form of hair foam, then a stable, micro-porous and creamy foam is formed that can be uniformly dispersed on the hair without dripping.

A third subject matter of the invention is a method for treating keratin-containing fibers, particularly human hair, wherein an agent according to the first subject matter is foamed to a foam by the use of a dispensing device, and the resulting foam is applied onto the keratin-containing fibers.

Preferably, the keratin-containing fibers are shaped and this shape is fixed by the agent of the first subject matter of the invention.

The abovementioned dispensing devices (see above) are inventively preferred.

A fourth subject matter of the invention is a method for treating keratin-containing fibers, especially human hair, wherein an agent according to the first subject matter is applied as a spray onto keratin-containing fibers by use of a dispensing device. It is preferred that the keratin-containing fibers are shaped and this shape is fixed by the agent of the first subject matter of the invention.

The abovementioned dispensing devices (see above) are inventively preferred.

The following examples are intended to illustrate the subject matter of the present invention in more detail, without limiting it in any way.

EXAMPLES

Unless otherwise stated, the quantities are understood to be in weight percent.

The following formulations were prepared by blending the listed raw materials:

| Raw Materials | A | B | C | E | F | G | H | I |
|---|---|---|---|---|---|---|---|---|
| Aquastyle ® 300 | 6.0 | 6.0 | 2.0 | 5.0 | 5.0 | 4.0 | 4.0 | 2.0 |
| Celquat ® L200 | 1.0 | 2.0 | 1.0 | — | — | 1.0 | 1.0 | — |
| Styleze ® W-10 | — | — | — | 4.0 | 4.0 | — | — | 3.5 |
| Styleze ® CC10 | — | — | — | — | — | 6.0 | 2.0 | 2.0 |
| Luviskol ® VA 64 W | 8.0 | — | — | 6.0 | — | — | — | — |
| Luviskol ® K 85 | — | 6.0 | — | — | 8.0 | — | — | — |
| Luviset ® Clear | — | — | 5.0 | — | — | — | — | — |
| Acudyne ® SCP | — | — | — | — | — | — | 3.0 | — |
| PEG-40 hydrogenated castor oil | 0.2 | 0.2 | 0.1 | 0.1 | 0.2 | 0.2 | 0.15 | 0.2 |
| Water | ad 100 | | | | | | | |

| Raw Materials | J | K | L | M | N | O | P | Q |
|---|---|---|---|---|---|---|---|---|
| Aquastyle ® 300 | 3.0 | 3.0 | 3.0 | 6.0 | 2.0 | 3.0 | 3.0 | 3.0 |
| Luviquat ® Supreme | 5.0 | 4.0 | — | — | — | — | — | — |
| Styleze ® W-10 | — | — | — | — | — | — | 4.0- | 4.0 |
| Gafquat ® 755 NPW | — | — | 5.0 | 2.0 | 5.0 | 5.0 | — | — |
| Luviskol ® VA 64 W | 6.0 | — | — | 5.0 | — | — | — | — |
| Luviskol ® K 85 | — | 6.0 | 5.0 | — | — | — | — | — |
| Luviset ® Clear | — | — | — | — | 6.0 | — | — | — |
| Styleze ® CC10 | — | — | — | — | — | 3.0 | 3.0 | 3.0 |
| PEG-40 hydrogenated castor oil | 0.2 | 0.2 | 0.1 | 0.1 | 0.2 | 0.1 | 0.2 | 0.2 |
| Water | ad 100 | | | | | | | |

Formulations A to Q were each filled into an aerosol container that meets the following technical parameter: aluminum reservoir container with valve product 522983 PV 10697 from the Precision Company (Deutsche Präzisions-Ventil GmbH).

The aerosol container was filled with a mixture of the propellant gases propane/butane (47 wt. % propane, 50 wt. % butane, 3 wt. % isobutene) so that the weight ratio of formulation to propellant gas was 92 to 8.

All formulations when applied onto the hair produced an outstandingly flexible hold to the hairstyle. The hair received very good care. When the formulations were deployed as aerosol foam, voluminous foam was obtained that broke down when first applied on the hair.

Index of raw materials:

Aquastyle® 300 copolymer of N-vinyl pyrrolidone/N-vinyl caprolactam/N-(3-dimethylaminopropyl)methacrylamide and 3-(methacryloylamino)propyl-lauryl-dimethylammonium chloride (active substance 30 wt. % in water/ethanol, INCI name: Polyquaternium-69) (ISP), Acudyne® SCP copolymer of acrylamide and sodium 2-acrylamido-2-methyl-1-propane sulfonate (ca. 25 to 27 wt. % active substance in water, INCI name: Acrylamide/Sodium Acryloyldimethyltaurate/Acrylic Acid Copolymer) (Rohm & Haas)

Celquat® L 200 quaternized cellulose derivative (INCI name: Polyquaternium-4) (National Starch)

Gafquat® 755 N PW dimethylaminoethyl methacrylate-vinyl pyrrolidone copolymer, quaternized with diethyl sulfate (ca. 19% solids in water; INCI name: Polyquaternium-11) (ISP)

Luviset® Clear vinyl pyrrolidone-methacrylamide-vinyl imidazole copolymer (19-21% solids in water; INCI name: VP/MethacrylamideNinyl Imidazole Copolymer) (BASF)

Luviskol® K85 polyvinyl pyrrolidone (ca. 20% solids in water; INCI name: PVP) (BASF)

Luviskol® VA 64 W copolymer of vinyl acetate and N-vinyl pyrrolidone (48-52% active substance in water, INCI name: VP/VA Copolymer) (BASF)

Luviquat® FC 370 3-methyl-1-vinyl imidazolium chloride-vinyl pyrrolidone copolymer (30:70) (38-42% solids in water; INCI name: Polyquaternium-16) (BASF)

Luviquat® Supreme vinyl pyrrolidone-methacrylamide-vinyl imidazole-vinyl imidazolium methosulfate copolymer (55:29:10:6) (19-21% solids in water; INCI name: Polyquaternium-68) (BASF)

Styleze® W-10 copolymer of N-vinyl pyrrolidone, N,N-dimethylaminopropylmethacrylamide and N,N-dimethyl-N-dodecylammoniopropylmethacrylamide chloride (ca. 9 to 11% active substance, INCI name: Polyquaternium-55) (ISP)

Styleze® CC 10 copolymer of N-vinyl pyrrolidone and N,N-dimethylaminopropylmethacrylamide (ca. 9 to 11% active substance, INCI name: VP/DMAPA Acrylates Copolymer) (ISP)

We claim:

1. Agent for treating keratin-containing fibers comprising, in a cosmetically acceptable carrier:

(a) at least one amphiphilic, cationic polymer comprising at least one structural unit according to Formula (I), at least one structural unit according to Formula (II), at least one structural unit according to Formula (III) and at least one structural unit according to Formula (IV),

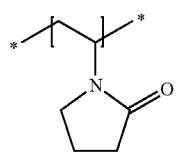 (I)

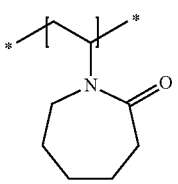 (II)

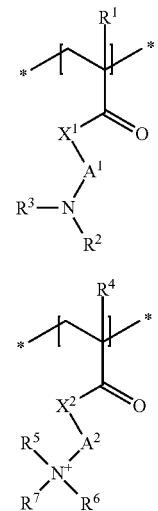 (III)

(IV)

wherein

R$^1$ and R$^4$ are, independently of one another, a hydrogen atom or a methyl group, X$^1$ and X$^2$ are, independently of one another, an oxygen atom or an NH group, A$^1$ and A$^2$ are, independently of one another, an ethane-1, 2-diyl, propane-1,3-diyl or butane-1,4-diyl group, R$^2$, R$^3$, R$^5$ and R$^6$ are, independently of one another, a (C$_1$ to C$_4$) alkyl group, R$^7$ is a (C$_8$ to C$_{30}$) alkyl group, and (b) at least one additional film-forming cationic and/or setting cationic polymer comprising at least one structural element according to Formula (M1)

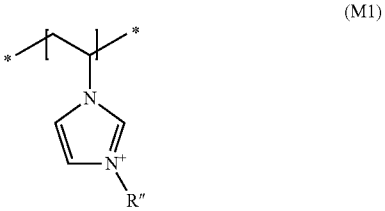 (M1)

wherein R" is a (C$_1$ to C$_4$) alkyl group, and a cationic and/or non-ionic structure, and (c) at least one film-forming non-ionic and/or setting non-ionic polymer chosen from polyvinyl pyrrolidone, copolymers of N-vinyl pyrrolidone and vinyl esters of carboxylic acids containing 2 to 18 carbon atoms, copolymers of N-vinyl pyrrolidone and N-vinyl imidazole and methacrylamide, copolymers of N-vinyl pyrrolidone and N-vinyl imidazole and acrylamide, and copolymers of N-vinyl pyrrolidone with N,N-di(C$_1$ to C$_4$) alkylamino (C$_2$ to C$_4$) alkylacrylamide.

2. Agent according to claim 1 wherein in Formula (III) and Formula (IV), respectively, R$^1$ and R$^4$ are a methyl group.

3. Agent according to claim 1 wherein in Formula (III) and Formula (IV), respectively, R$^2$, R$^3$, R$^5$ and R$^6$ are, independently of one another, methyl or ethyl.

4. Agent according to claim 1 wherein in Formula (IV), R$^7$ is a (C$_{10}$ to C$_{24}$) alkyl group.

5. Agent according to claim 4 wherein in Formula (IV), R$^7$ is decyl (caprinyl), dodecyl (lauryl), tetradecyl (myristyl), hexadecyl (cetyl), octadecyl (stearyl), eicosyl (arachyl) or docosyl (behenyl).

6. Agent according to claim 1 wherein the at least one amphiphilic, cationic polymer comprises at least one structural unit of Formula (I), at least one structural unit of Formula (II), at least one structural unit of Formula (III-8) and at least one structural unit of Formula (IV-8)

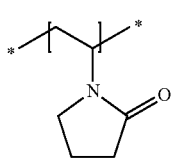 (I)

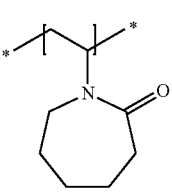 (II)

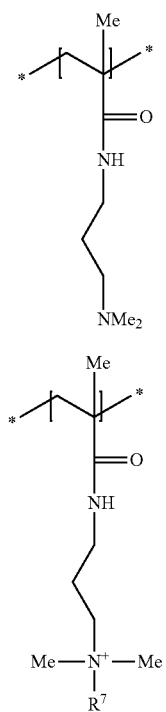

wherein R⁷ is octyl (capryl), decyl (caprinyl), dodecyl (lauryl), tetradecyl (myristyl), hexadecyl (cetyl), octadecyl (stearyl), eicosyl (arachyl) or docosyl (behenyl).

7. Agent according to claim 1 wherein the at least one amphiphilic, cationic polymer is present in the agent in an amount of 0.1 wt. % to 20.0 wt. %, based on total weight of the agent.

8. Agent according to claim 1 wherein the at least one film-forming cationic and/or setting cationic polymer further comprises at least one cationic, quaternized cellulose derivative.

9. Agent according to claim 1 wherein the at least one film-forming cationic and/or setting cationic polymer further comprises at least one structural unit of Formula (I), at least one structural unit of Formula (VI), and optionally at least one structural unit of Formula (V)

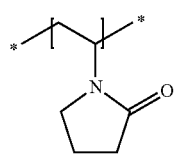

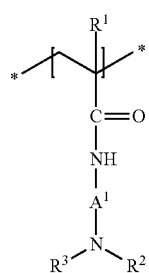

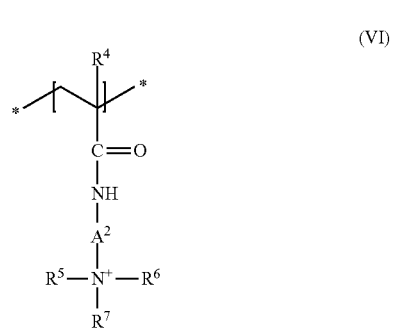

wherein $R^1$ and $R^4$ are, independently of one another, a hydrogen atom or a methyl group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, and $R^7$ is a ($C_8$ to $C_{30}$) alkyl group.

10. Agent according to claim 1 wherein the film-forming non-ionic and/or setting non-ionic polymers are comprised in an amount of 0.1 wt. % to 20.0 wt. %, based on the weight of the agent according to the invention.

11. Agent according to claim 1 further comprising at least one propellant.

12. Agent according to claim 1 wherein it is in the form of an aerosol foam or aerosol spray.

13. Method for treating keratin-containing fibers, comprising foaming an agent according to claim 1 to foam by a dispensing device, and applying the resulting foam onto the keratin-containing fibers.

14. Method for treating keratin-containing fibers, comprising spraying an agent according to claim 1 onto the keratin-containing fibers by a dispensing device.

* * * * *